United States Patent
List et al.

(10) Patent No.: US 8,251,922 B2
(45) Date of Patent: Aug. 28, 2012

(54) ANALYSIS SYSTEM FOR AUTOMATIC SKIN PRICK ANALYSIS

(75) Inventors: Hans List, Hesseneck-Kailbach (DE);
Hans-Peter Haar, Weisloch (DE);
George Bevan Kirby Meacham, Shaker Heights, OH (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 163 days.

(21) Appl. No.: 12/755,839

(22) Filed: Apr. 7, 2010

(65) Prior Publication Data

US 2011/0092855 A1    Apr. 21, 2011

Related U.S. Application Data

(63) Continuation of application No. PCT/EP2008/008435, filed on Oct. 7, 2008.

(60) Provisional application No. 60/978,268, filed on Oct. 8, 2007.

(51) Int. Cl.
*A61B 5/00* (2006.01)
*B65D 81/00* (2006.01)

(52) U.S. Cl. ...................................... 600/584; 600/583

(58) Field of Classification Search ............... 600/583, 600/584; 606/181–183
See application file for complete search history.

(56) References Cited

U.S. PATENT DOCUMENTS

| | | | |
|---|---|---|---|
| 5,318,584 | A | 6/1994 | Lange et al. |
| RE35,803 | E | 5/1998 | Lange et al. |
| 7,288,073 | B2 | 10/2007 | Effenhauser et al. |
| 2008/0108910 | A1 | 5/2008 | Hein et al. |
| 2008/0249435 | A1 | 10/2008 | Haar et al. |
| 2008/0262388 | A1 | 10/2008 | List et al. |

FOREIGN PATENT DOCUMENTS

| | | |
|---|---|---|
| EP | 0565970 B1 | 9/1997 |
| EP | 1360933 A1 | 11/2003 |
| EP | 1709906 A1 | 10/2006 |
| EP | 2030567 A1 | 3/2009 |
| WO | 01/72220 A1 | 10/2001 |
| WO | 03/009759 A1 | 2/2003 |
| WO | 03/088835 A2 | 10/2003 |
| WO | 2005/084546 A2 | 9/2005 |
| WO | 2005/110227 A1 | 11/2005 |
| WO | 2006/059232 A1 | 6/2006 |
| WO | 2007/045412 A1 | 4/2007 |
| WO | 2007/073870 A2 | 7/2007 |
| WO | 2008/131920 A2 | 11/2008 |
| WO | 2009/030340 A1 | 3/2009 |

OTHER PUBLICATIONS

International Search Report and Written Opinion from Corresponding PCT/EP2008/008435, Mar. 27, 2009.

*Primary Examiner* — Max Hindenburg
*Assistant Examiner* — Jonathan M Foreman
(74) *Attorney, Agent, or Firm* — Kristina E. Swanson; Roche Diagnostics Operations, Inc.

(57) ABSTRACT

Analysis system for automatically performing a skin prick analysis by pricking the skin for producing a sample of body liquid and detecting an analyte contained in the sample. The analysis system comprises a magazine with a plurality of compartments each containing a lancing element and an analysis element, and a reusable hand-held instrument having a drive assembly. The drive assembly is adapted for driving at least the following movements by manually generated mechanical force: a coupling movement by which one of the lancing elements is coupled to the drive assembly; a puncturing and sample collection movement of one of the lancing elements contained in the magazine and coupled to the drive assembly; and a remaganizing movement by which the test element is transported back into the compartment of the magazine.

19 Claims, 19 Drawing Sheets

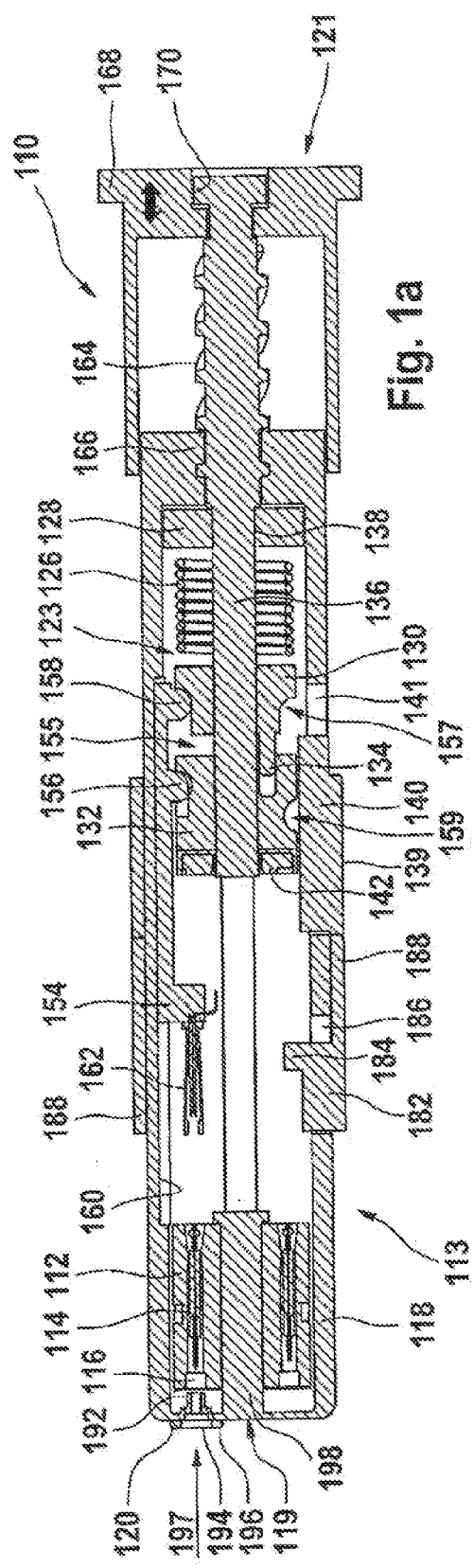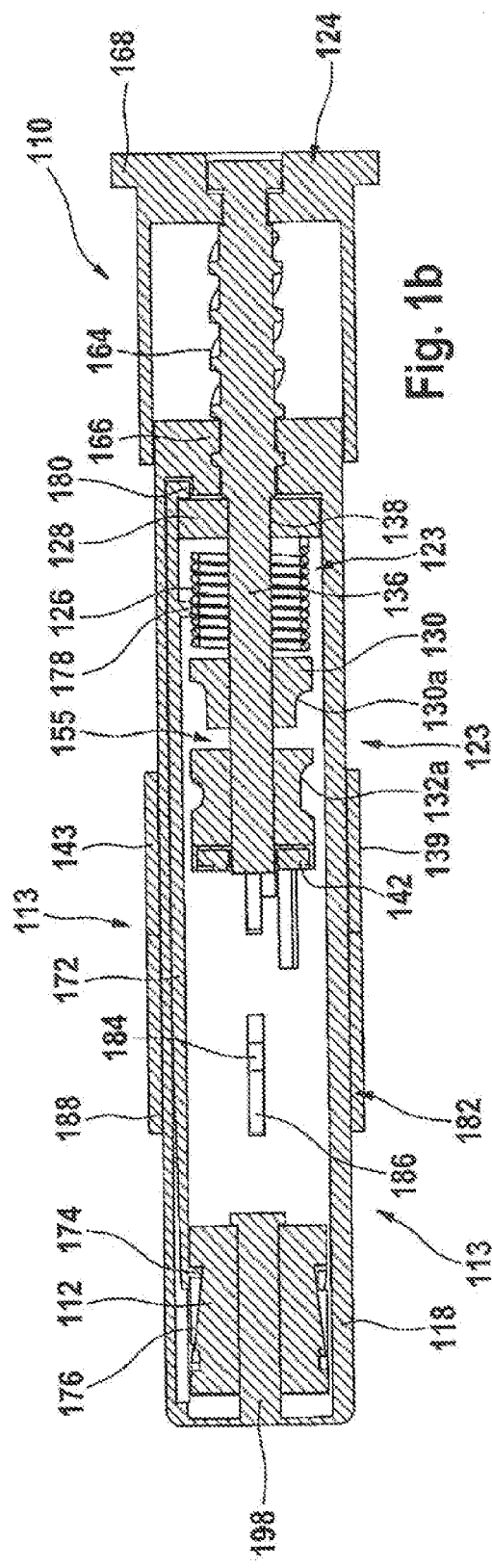

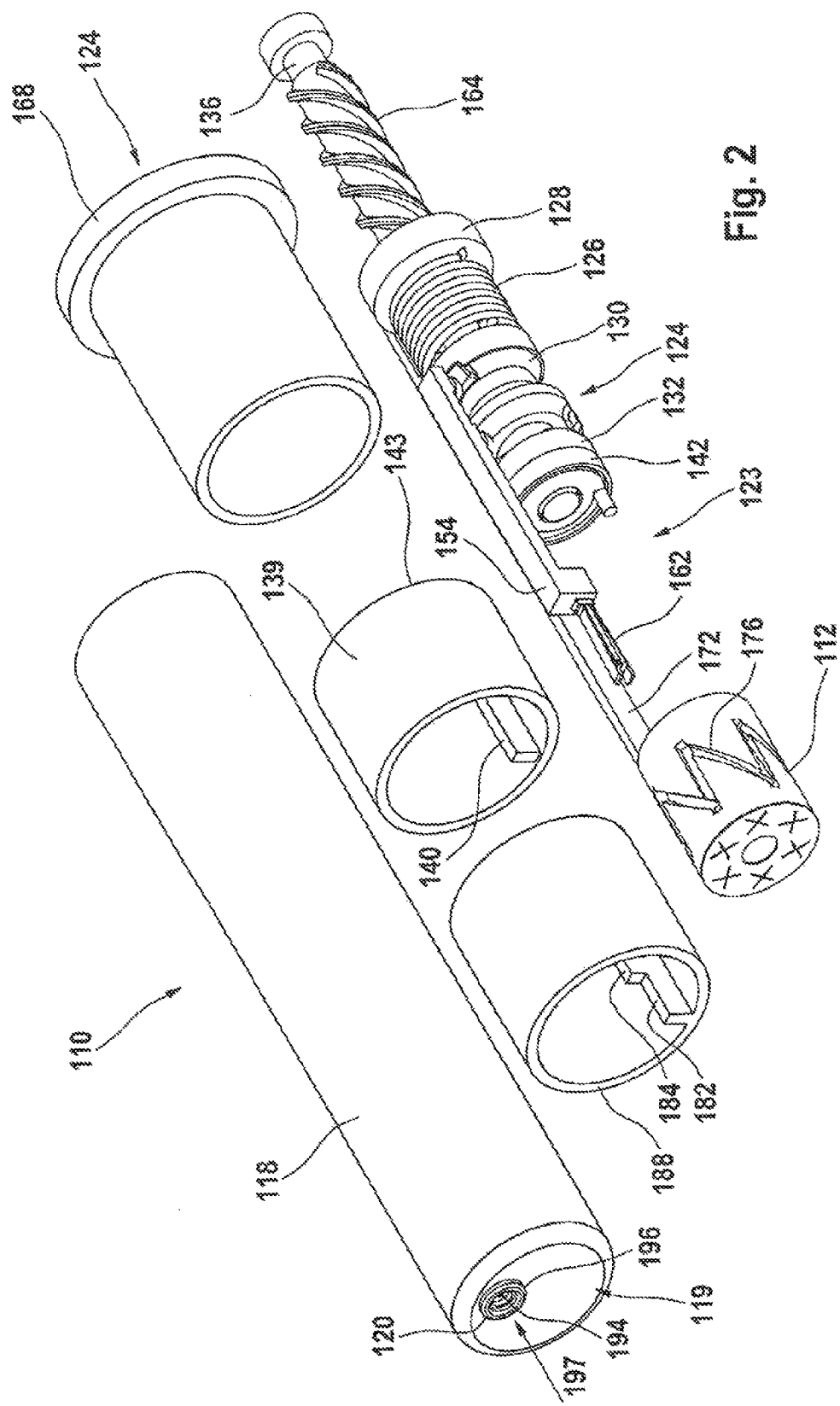

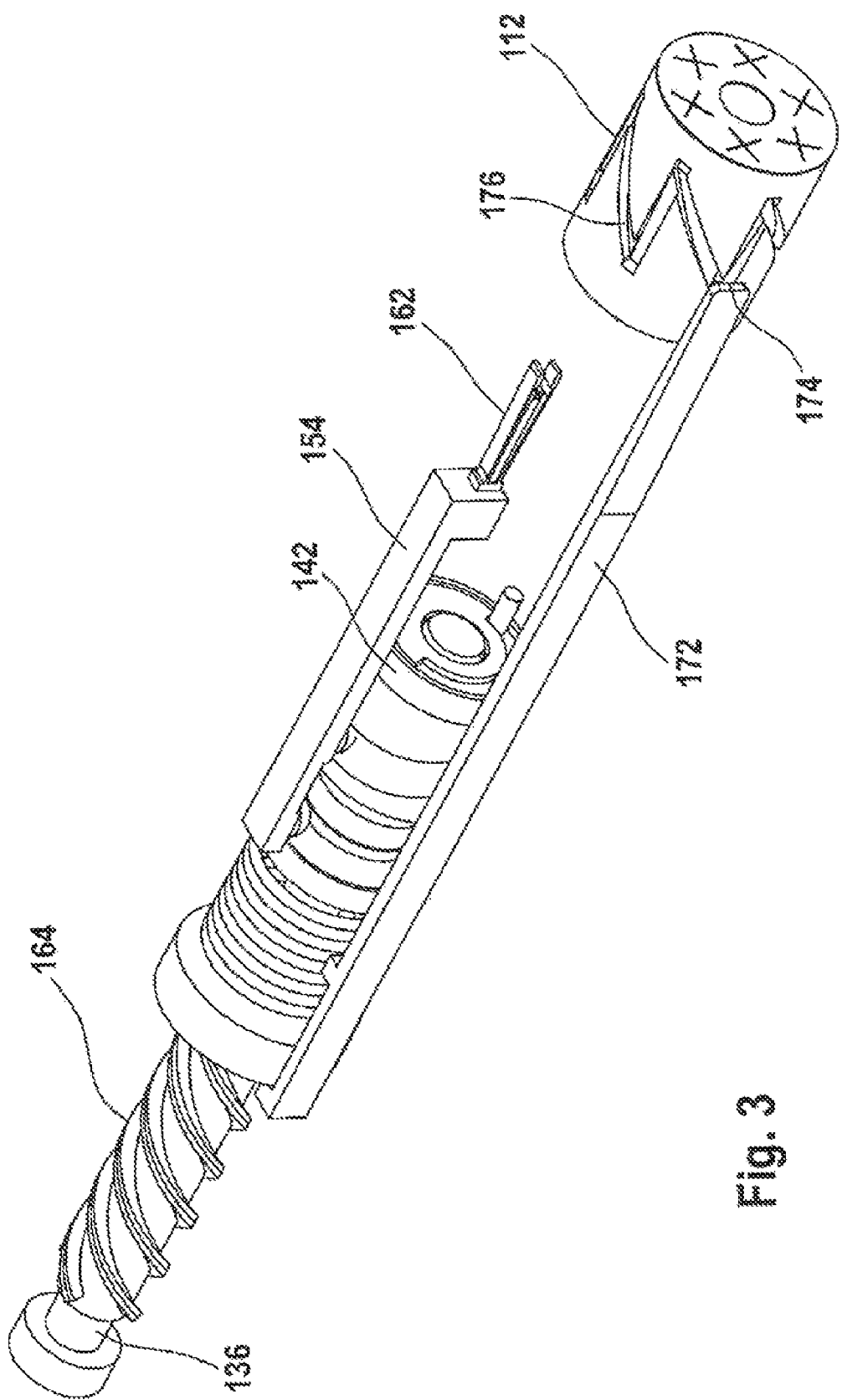

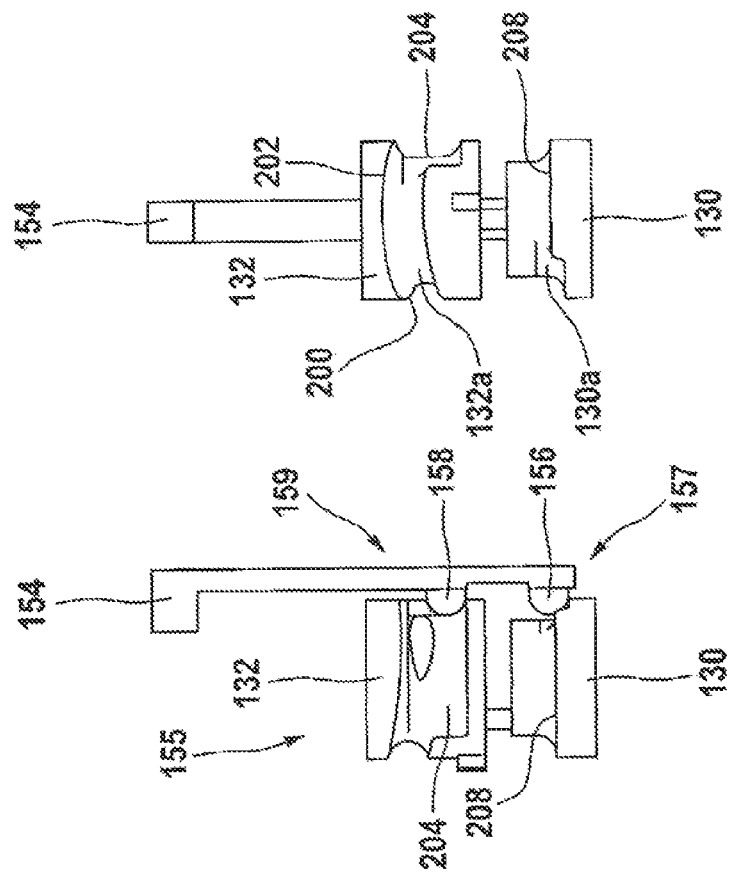
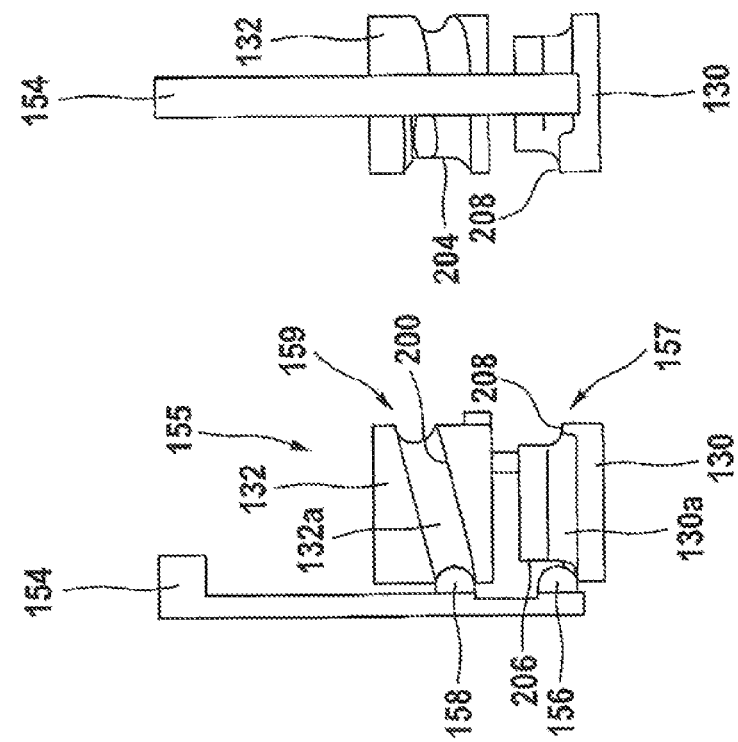

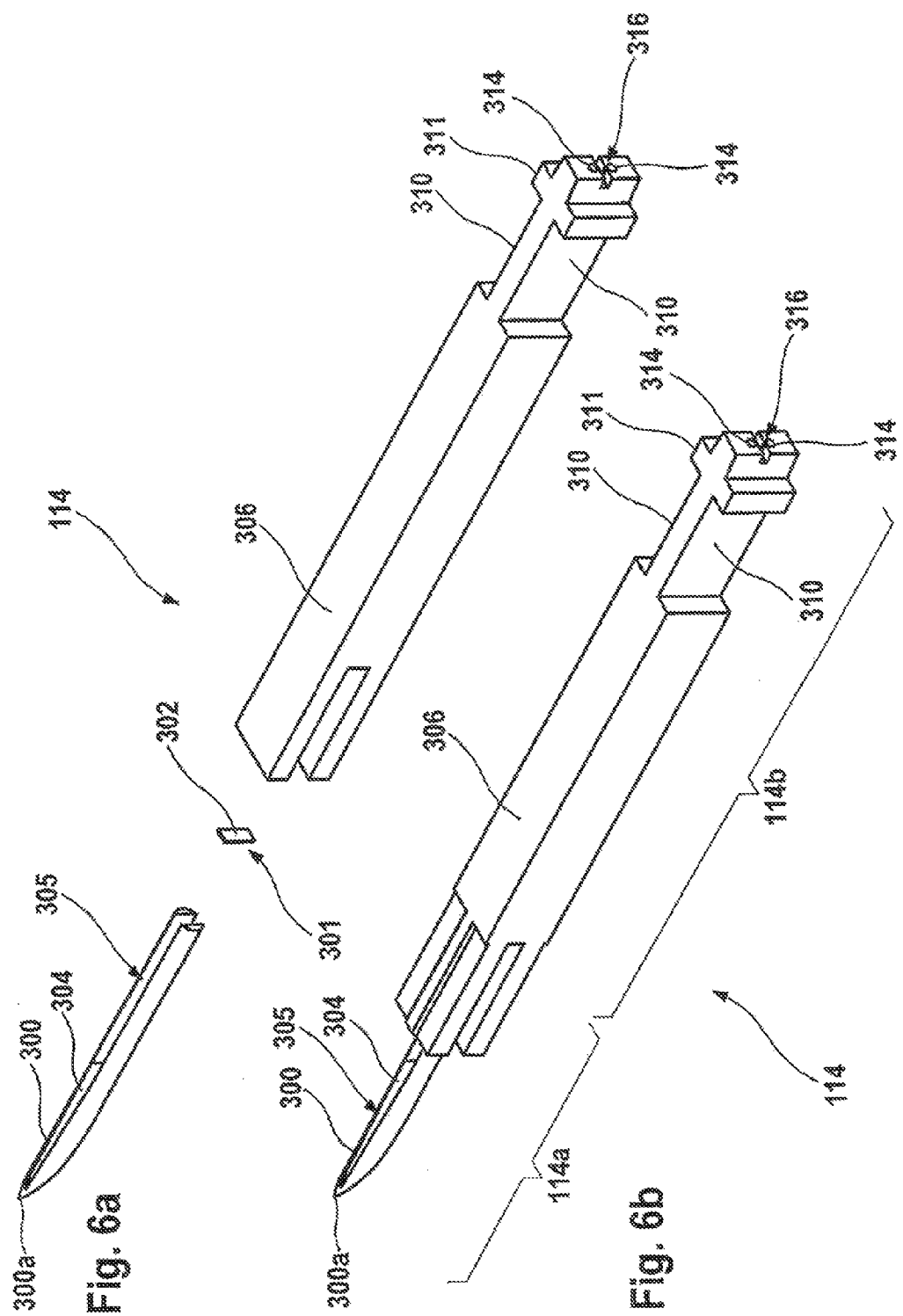

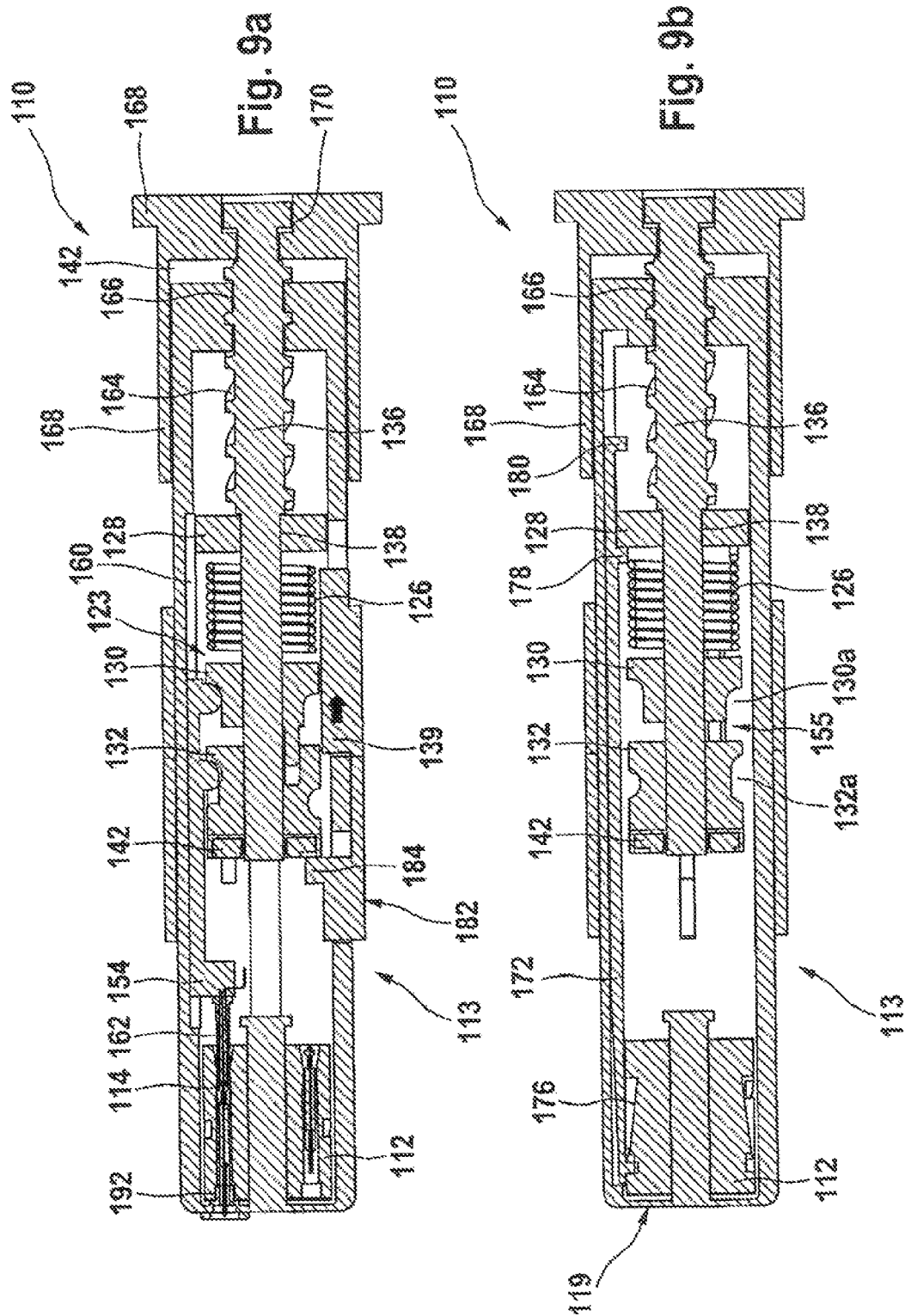

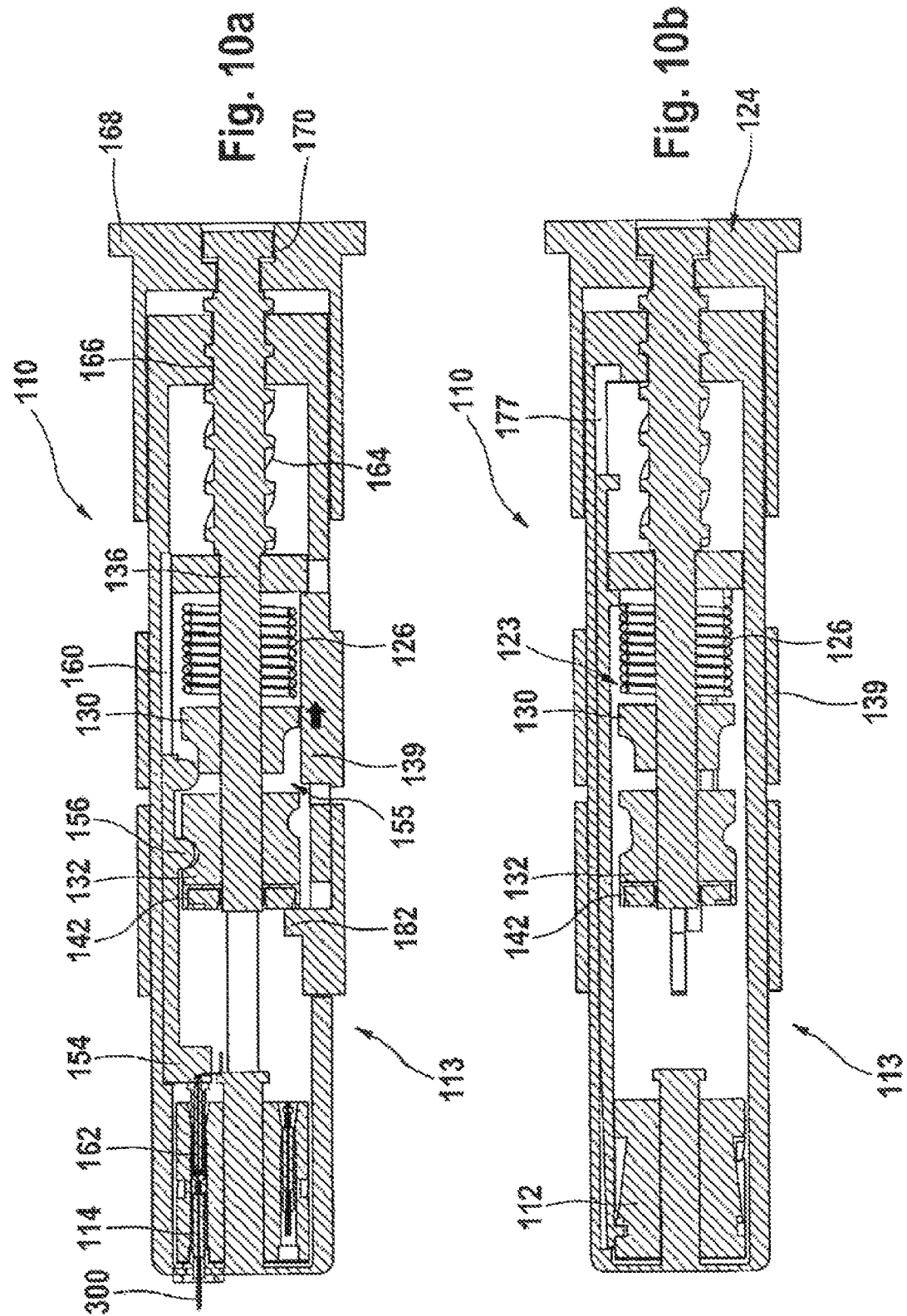

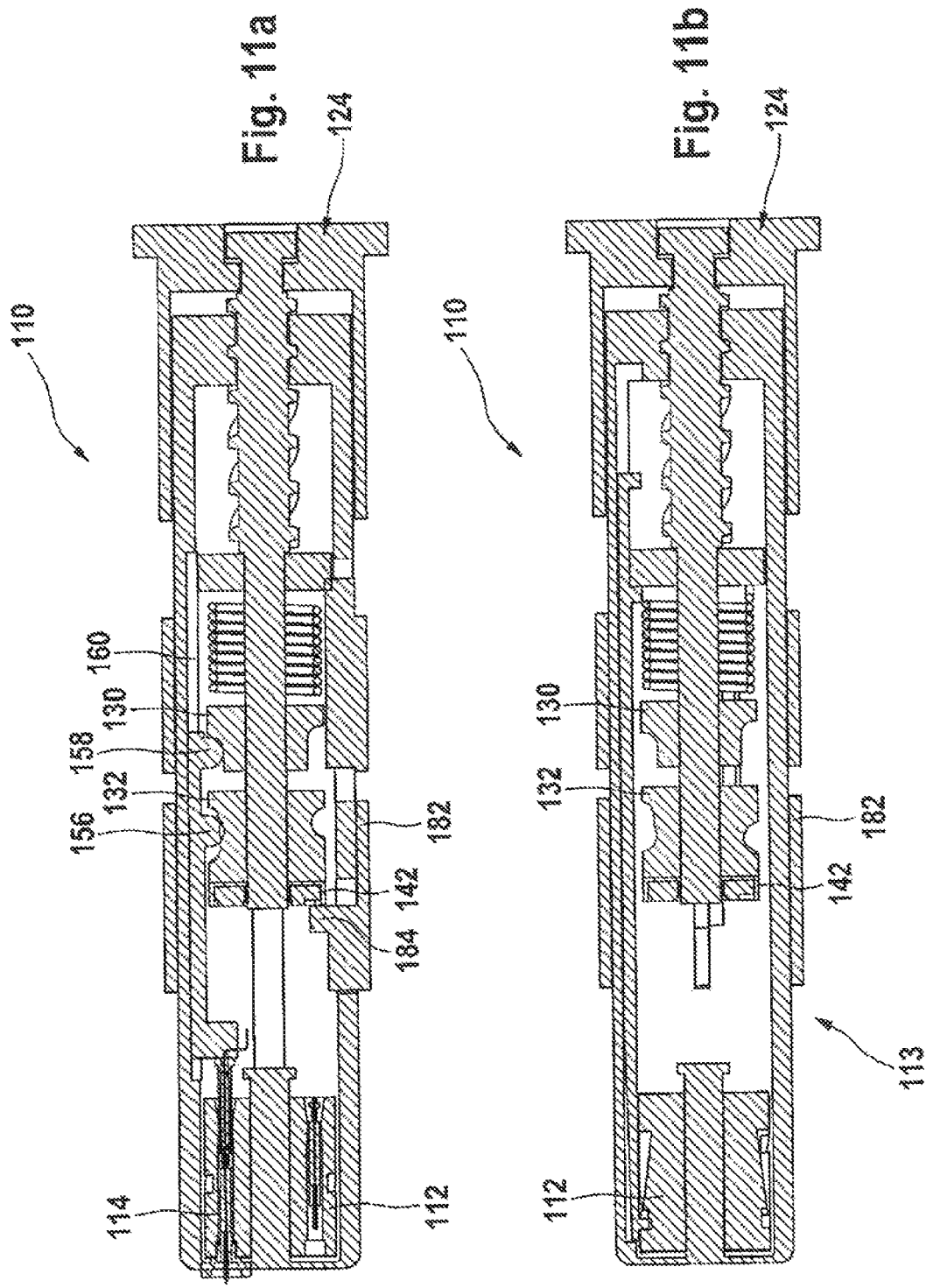

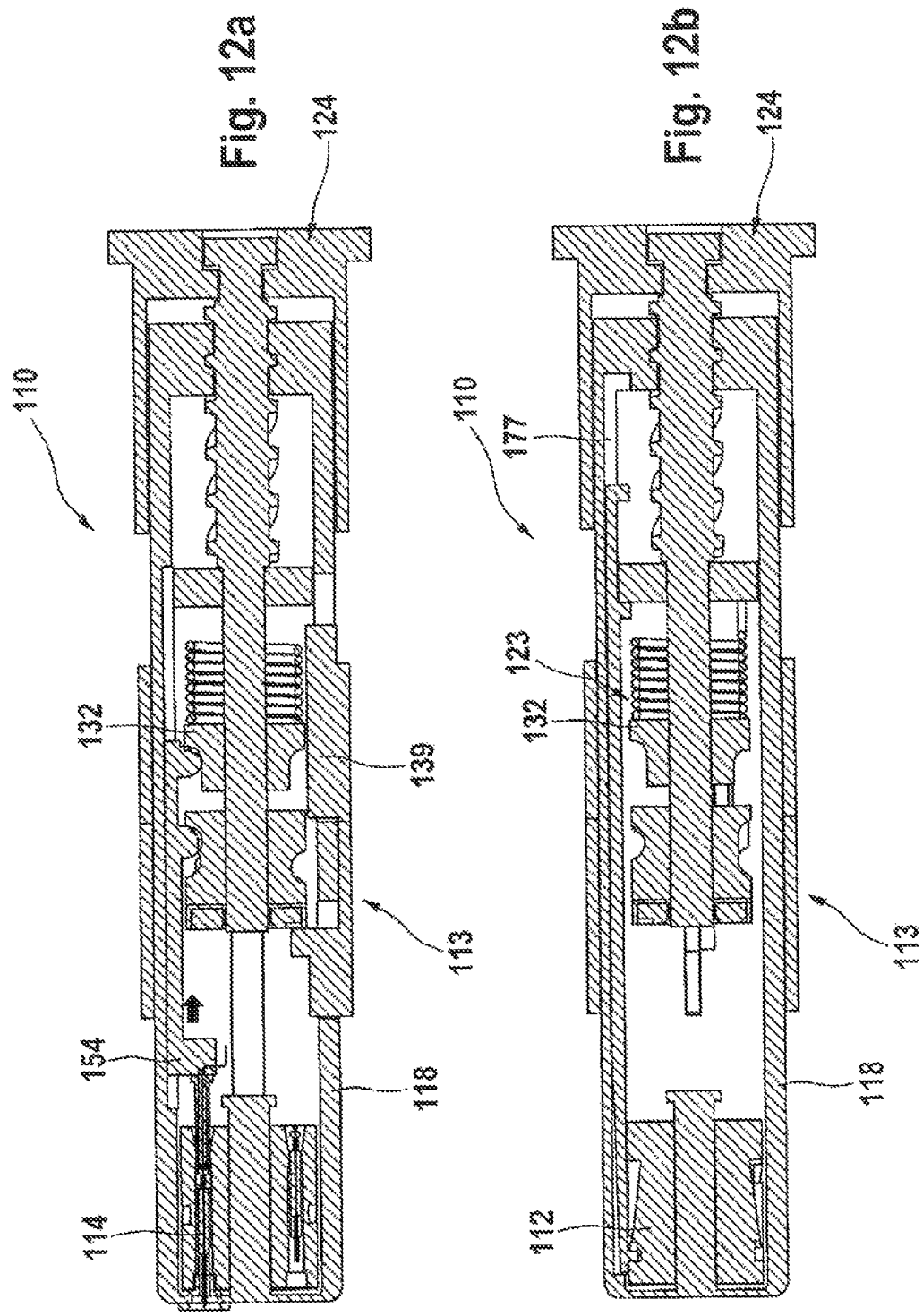

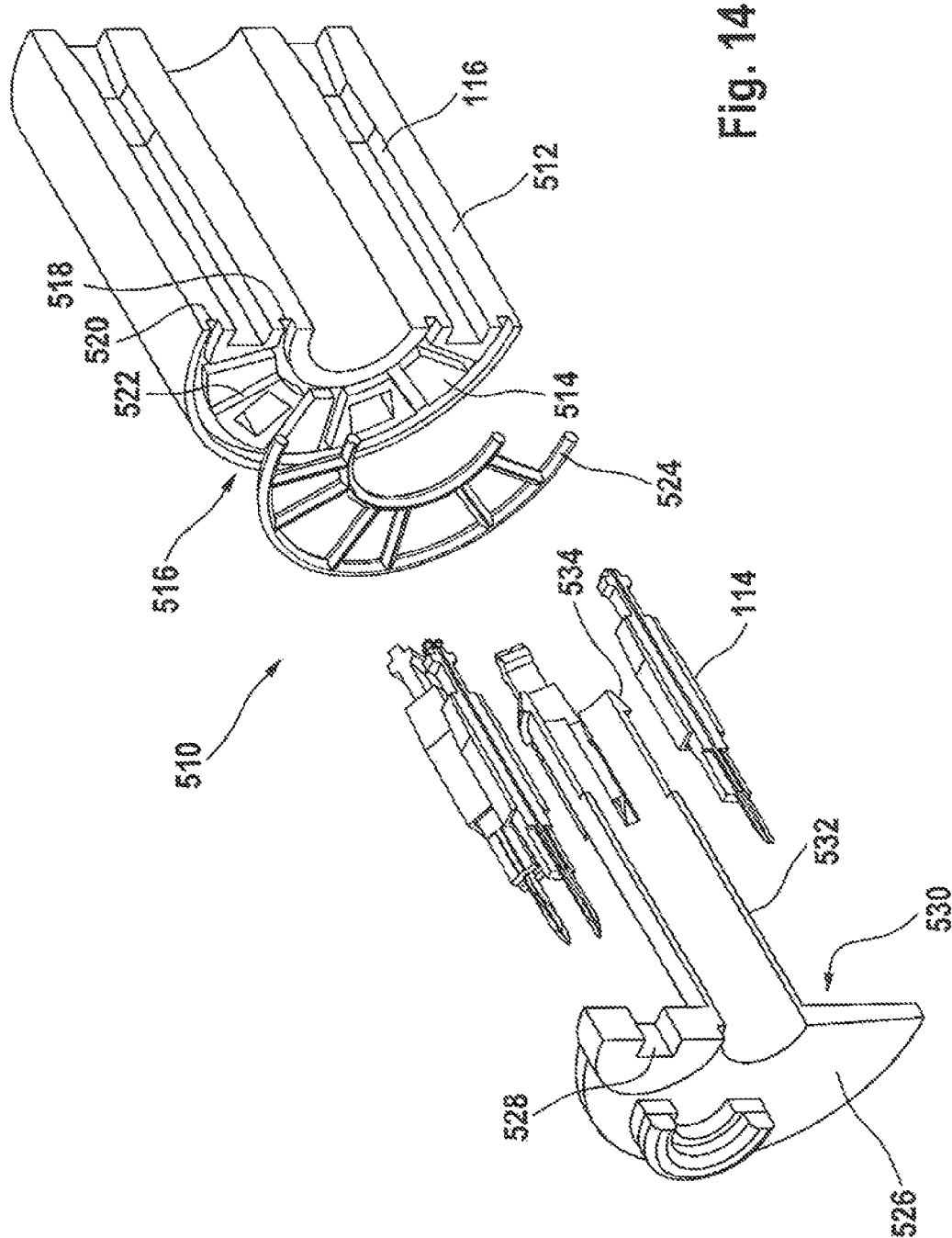

ANALYSIS SYSTEM FOR AUTOMATIC SKIN PRICK ANALYSIS

CROSS-REFERENCE TO RELATED APPLICATIONS

This application is a continuation of PCT/EP2008/008435, filed Oct. 7, 2008, which is based on and claims priority to U.S. Provisional Application Ser. No. 60/978,268, filed Oct. 8, 2007, which is hereby incorporated by reference.

BACKGROUND

The present disclosure generally relates to a system suitable for automatically performing a skin prick analysis and, in particular, relates to a system suitable for automatically performing a skin prick analysis by pricking the skin of a human, or animal, subject to produce a sample of body liquid and to detect the presence, or concentration, of one or more constituents, or analytes, in the sample liquid. Depending on the skin site used and on the lancing depth, the body liquid can be blood or interstitial liquid or a mixture thereof.

Analysis based on skin-piercing can be important in several fields of medical diagnostics and treatment. One area of particular importance is the field of diabetes management. It has been determined that severe long term damages caused by diabetes mellitus can be avoided if the patient can control her/his blood sugar level several times a day in order to adapt the required insulin injections closely to the actual need for maintaining a constant blood sugar level. This control requires so called "home-monitoring" by the patient himself, or by other people not having a medical training.

Analysis systems used in this context generally comprise a particular type of disposable analysis element, such as, for example a test strip, and an instrument adapted to the analysis element and suitable for evaluating results of an analytical reaction occurring therein. The analysis element can include a reagent system which reacts with the analyte contained in the sample, thereby producing a measurable change of a measurement quantity characteristic for the desired analytical result. Generally, two types of such analysis systems are known, namely optical systems in which the measurement quantity is a color change, or other optically measurable quantity, and electrochemical systems in which the measurement quantity is an electrical current or other electrically measurable quantity. The change of the measurement quantity resulting from the reaction can be measured and evaluated by the instrument belonging to the analysis system, thereby producing the desired analytical result.

In addition to diabetes management, other important fields of medical diagnostics and treatment with similar requirements, including home-monitoring, exist. These can refer, for example, to the regular control of blood cholesterol and to the control of blood coagulation parameters. Similar situations can also exist, e.g., in so called "near-patient-testing".

In earlier skin prick analysis systems, a plurality of steps typically had to be performed by the user, including a skin prick step, using a lancing instrument, and a separate analysis step, using an analysis element of the analysis system. Between the two steps, a transfer of the sample from the skin to the analysis element was necessary.

In order to overcome the problems caused by the complicated two step-handling, automatic skin prick analysis systems have been developed. Such systems can allow the performance all steps required for the skin prick analysis in a fully automatic operation in particular without any sample transfer handling steps of the user. Occasionally, such systems are designated "G&M-systems" because they allow the "getting" (G) of the required sample and the "measuring" (M) of the desired analytical value without user intervention.

Most G&M-systems operate with an integral lancing and analysis element, also designated as "test element". The two components of such test elements, a lancing element and an analysis element, are generally manufactured separately but assembled by the manufacturer or at least before use, i.e., before the lancing movement is triggered. In the instrument belonging to the system such elements are processed as a unified item. In other G&M systems, separate lancing and analysis elements are provided and processed separately during at least a part of the analytical procedure.

These known approaches reflect a basic problem of G&M systems, namely the complexity of the handling steps required for a fully automatic analysis. Some of the prior art approaches concentrate only on a particular design of test element, such as, for example, integral lancing and analysis element, but provide no solution to how the test elements should be handled in a comfortable manner by an instrument belonging to the respective analysis system. For example, such prior art systems require that the test element be manually inserted into the instrument for each analysis.

Some systems provide a more comfortable solution by using a cartridge or magazine containing a plurality of test elements. Such systems provide an improved comfort because a plurality of analyses can be performed automatically without a need for the user to perform any manual handling steps other than pressing the instrument to her or his finger or other body part and triggering the operation of the instrument. However, these systems require generally a large volume and weight in order to allow for the electromechanical realization of all the movement steps required for a fully automatic analysis.

It has been found one important improvement regarding the contradictory requirements of user comfort, on the one hand, and small size and weight, on the other hand, can be achieved if movements required inside the instrument for automatically performing the analysis are driven by manually generated force, i.e. without an electric motor or consumption of electrical energy, using only a small battery for measurement—and evaluation electronics.

Therefore, there is a need for an improved system for automatically performing a skin prick analysis with maganized lancing elements.

SUMMARY

According to the present disclosure, an analysis system for automatically performing a skin prick analysis by pricking the skin for producing a sample of body liquid and detecting an analyte contained in the sample is presented. The analysis system comprises a magazine with a plurality of compartments each containing a lancing element and an analysis element. The lancing element has a pricking tip for performing a skin prick and a sample transfer capillary for transfer of sample liquid to the analysis element. The analysis element comprises a reagent system which reacts with the analyte contained in the sample causing a measurable change of a measurement quantity characteristic of the desired analytical result. The analysis system also comprises a reusable hand-held instrument having a housing and a drive assembly for driving movements of parts inside the housing as required for the analysis. The drive assembly drives at least the following movements by manually generated mechanical force: (a) a coupling movement by which one of the lancing elements, which is in a compartment of the magazine in a piercing position, is coupled to the drive assembly for being driven thereby and (b) a puncturing and sample collection movement of one of the lancing elements contained in the magazine and coupled to the drive assembly. The movement includes a forward movement phase in a puncturing direction until the pricking tip reaches a point of maximum displacement and, after the point of maximum displacement, a reverse movement phase opposite to the puncturing direction during which reverse movement phase the speed is reduced as compared to the forward movement for allowing suctioning of sample into the sample transfer capillary. In addition, the drive assembly may drive a remaganizing movement by which the test element is transported back into the same compartment of the magazine.

In accordance with one embodiment of the present disclosure, the drive assembly may also drive by manually generated mechanical force an indexing movement of the magazine for transporting a compartment thereof containing an unused disposable test element to the piercing position.

In accordance with one embodiment of the present disclosure, the electrical power required by the analysis system can be provided by a small battery of less than approximately 2-3 $cm^3$ and/or less than approximately 10-15 g weight Accordingly, it is a feature of the embodiments of the present disclosure to a fully automatic finger prick analysis system with a pen-like size and shape that has a very precise control of the lancing action including all required movements. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIGS. 1a-b illustrate sectional views of an analysis system according to an embodiment of the present disclosure.

FIG. 2 illustrates sectional an exploded perspective view of parts of the analysis system according to an embodiment of the present disclosure.

FIG. 3 illustrates a perspective view of interior parts of the analysis system according to an embodiment of the present disclosure.

FIGS. 5a-d illustrate elevational views of a cam controller with cam rotors and corresponding cam followers according to an embodiment of the present disclosure.

FIG. 6a illustrates a perspective view of a test element of the analysis system according to an embodiment of the present disclosure.

FIG. 6b illustrates an exploded view of the test element according to an embodiment of the present disclosure.

FIGS. 9a-c illustrate sectional and cross-sectional views similar to FIGS. 1a-c but in a different operational status of the system m according to an embodiment of the present disclosure.

FIGS. 10a-c illustrate sectional and cross-sectional views similar to FIGS. 1a-c in a second different operational status of the system according to an embodiment of the present disclosure.

FIGS. 11a-c illustrate sectional and cross-sectional views similar to FIGS. 1a-c in a third different operational status of the system according to an embodiment of the present disclosure.

FIGS. 12a-c illustrate sectional and cross-sectional views similar to FIGS. 1a-c in a fourth different operational status of the system according to an embodiment of the present disclosure.

FIG. 14 illustrates a perspective exploded view of a magazine and test elements of the embodiment shown in FIG. 13 according to an embodiment of the present disclosure.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The system requirements of user comfort, on the one hand, and small size and weight, on the other hand, can be achieved if movements required inside the instrument for automatically performing the analysis are driven by manually generated force, i.e. without an electric motor or consumption of electrical energy. Ideally the instrument requires electrical energy only for its measurement—and evaluation electronics. In this system, the energy consumption can be designed to be very low and the required electrical power can be provided by a very small battery (typically a button cell) of less than approximately 2-3 $cm^3$, and/or less than approximately 10-15 g weight. In one embodiment, the small and/or low weight battery can be the only electrical energy source of the system. The electric energy consumption of the instrument can be so low that at least approximately 1000 analyses can be performed with a single battery. This number of analyses is generally considered a typical average lifetime of the system. Thus a preferred system comprises a "lifetime battery" which needs not be changed during its normal lifetime.

Figure 1C:
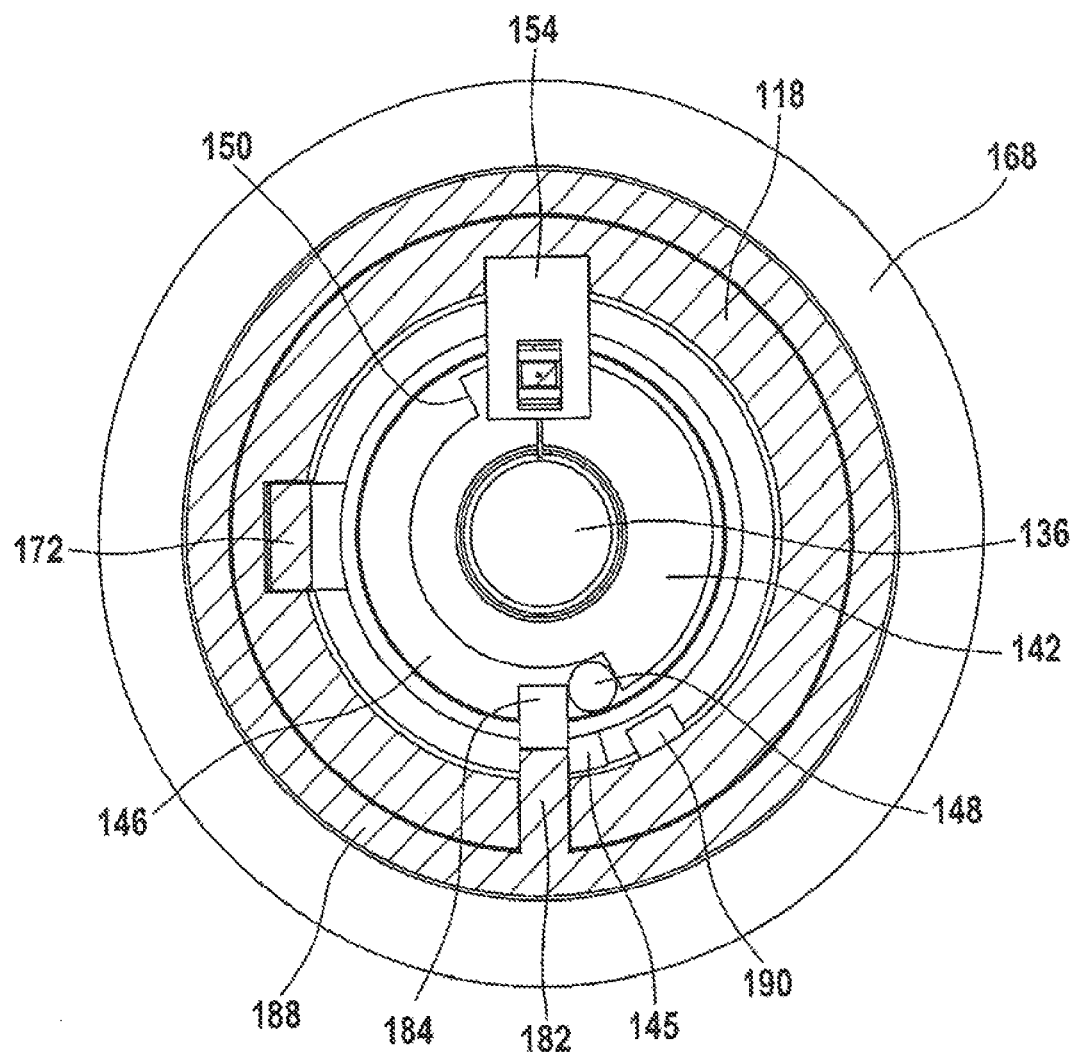
FIG. 1c illustrates a cross-sectional view of the system illustrated in FIGS. 1a and 1b according to an embodiment of the present disclosure.

Hereafter figures designated by both a number and letter are collectively referred to by the number only, e.g. FIGS. 1a to 1c are collectively designated FIG. 1.

Referring initially to FIG. 1, an analysis system 110 can comprises a magazine 112 and an instrument 113. The instrument 113 can have a housing 118. The magazine 112 can contain six test elements 114, wherein each test element can be housed in a separate compartment 116. The magazine 112 and the test elements 114 will be described in more detail below.

The instrument 113 can have a front end 119 with a skin contact surface 120 adapted to be pressed against the skin.

The instrument 113 can have a slim elongate shape ("pencil-type"), having a rear end 121 opposite to the front end 119. Hereafter, the term "forward" is used to designate a direction from the rear end towards the front (coinciding with the puncturing direction) end, whereas "rearward" is used to designate the opposite direction.

The instrument 113 can comprise a drive assembly 123 for driving a plurality of movements by manually generated force. The drive assembly 123 can comprise a torsion power spring 126, which can connect a spring input member 128 to a sample hold cam rotor 130. The sample hold cam rotor 130 can engage a lancing cam rotor 132 with a rotational link 134 such that the sample hold cam rotor 130 and the lancing cam rotor 132 can rotate in unison about a spindle 136, but the lancing cam rotor 132 can be adjusted axially relative to the sample hold cam rotor 130. The lancing cam rotor 132 can further comprise a trigger lug 145 (FIG. 1c).

A one-way clutch (not shown) at the interface 138 between the spring input member 128 and the spindle 136 can prevent reverse rotation of the spring input member 128 relative to the spindle 136. A release trigger 139 can engage the trigger lug 145 of lancing cam rotor 132 and can prevent forward rotation of the linked sample hold cam rotor 130 and the lancing cam rotor 132, thereby countering the torque of the torsion power spring 126 until it can be moved by the user to initiate the lancing action. The release trigger 139 can comprise a lug 140 sliding in an axial slot 141 in the housing 118 and a guide ring 143 sliding on the outer diameter of the housing 118.

Figure 4:
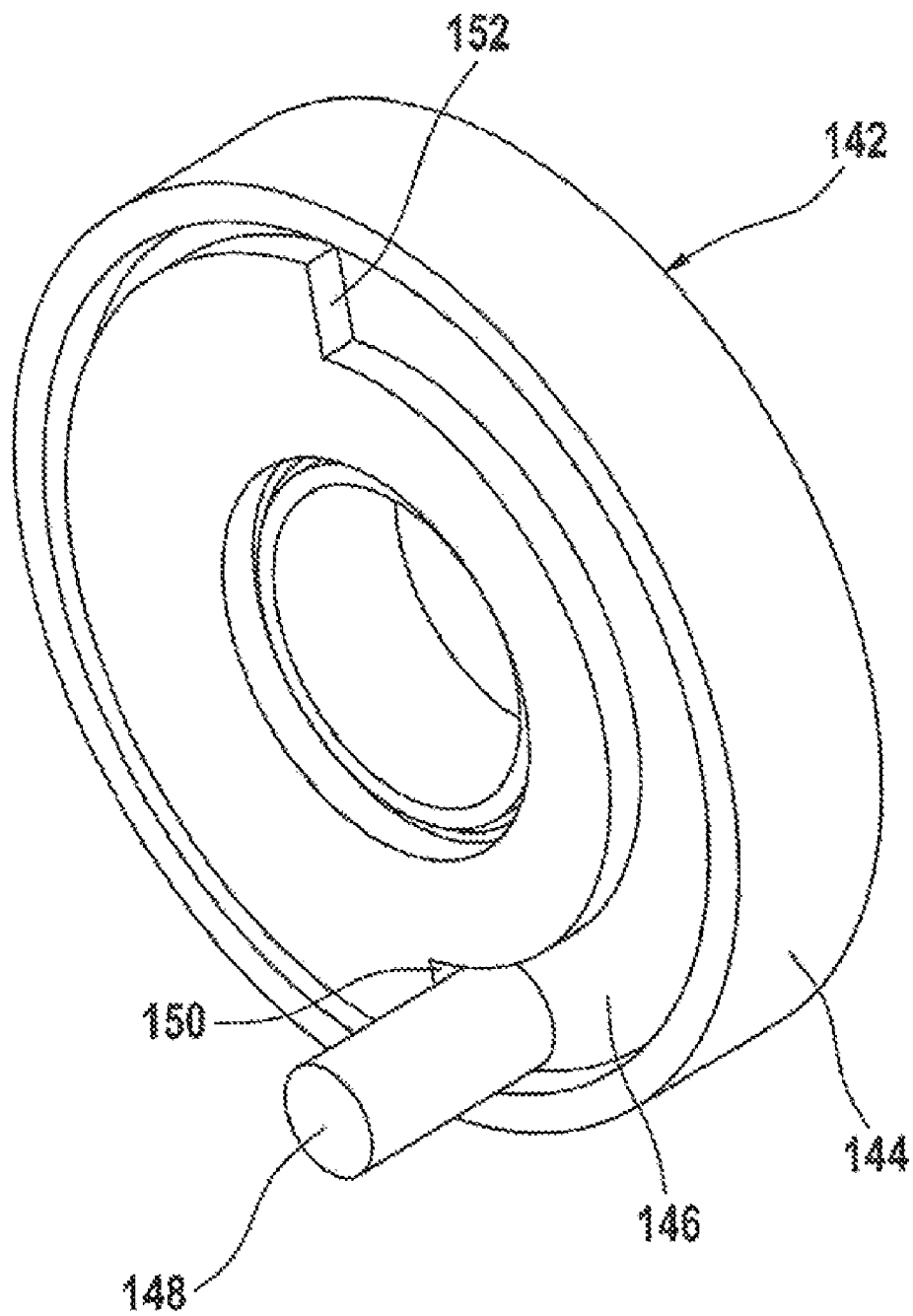
FIG. 4 illustrates a perspective view of a rotary time delay damper of the analysis system according to an embodiment of the present disclosure.

A rotary time delay damper 142 can be fixed to the front end of the lancing cam rotor 132 such that its rotation axis can coincide with the rotation axis of the lancing cam rotor 132. As shown in more detail in FIG. 4, the time delay damper 142 can comprise an outer housing 144, an inner rotating member 146, and a coupling pin 148 affixed to the inner rotating member 146. Limit stops 150 and 152 can be affixed to the outer housing 144 and can engage the coupling pin 148 such that the rotation of the coupling pin 148 and the inner rotating member 146 can be limited to a maximum rotation range of e.g., about 170 degrees. The inner rotating member 146 can be coupled to the outer housing 144 by a viscous material, e.g., silicone grease. Thereby, an angular velocity-dependent torque can be generated between the inner rotating member 146 and the outer housing 144. Further, the time delay damper 142 can comprise a torsional bias spring (not shown) that can turn the inner rotating member such that the coupling pin 148 can engage limit stop 150 when no other load is applied.

Further, the analysis system 110 can comprise a cam slider 154 incorporating a sample-hold cam follower 156 and a lancing cam follower 158 that can respectively engage cam recesses 130a,132a of the sample-hold cam rotor 130 and the lancing cam rotor 132. The cam slider 154 can slide axially in a channel 160 formed in the housing 118, such that it can execute linear axial motions when the sample-hold cam rotor 130 and the lancing cam rotor 132 rotate or move axially. A combined gripper and optical coupling 162 can be affixed to the cam slider such that it can be aligned to enter a compartment 116 in drum magazine 112 and can engage and move a test element 114. A low-force spring (not shown) can bias the cam follower in the rearward direction to assure contact between the sample-hold cam follower 156 and the sample-hold cam rotor 130.

The two cam rotors 130, 132 and the two earn followers 156,158 together can form a cam controller 155 comprising two cam drive mechanisms, namely a sample hold cam drive mechanism 157 and a lancing cam drive mechanism 159. Elements of the cam controller 155 and the cam slider 154 are shown in more detail in FIG. 5.

The cam recess 132a of the lancing cam rotor 132 can comprise a lift ramp 200 that can contact the lancing cam follower 158 and can accelerate the cam slider 154 forward to cause the test element 114 to penetrate the skin as the cam rotors rotate. It can further comprise a return ramp 202 that can stop the test element 114 and can accelerate it back out of the skin, and a clearance zone 204 that does not contact the lancing cam follower 158 so that the sample hold cam follower 156 can contact the cam recess 130a of sample hold cam rotor 130 and can control the motion of the test element 114 during the sample collection process. The sample hold cam recess 130a can comprise a clearance zone 206 that does not contact the sample hold cam follower 156, so that the lancing cam follower 158 can contact the lancing cam-rotor 132 and can control the motion of the test element 114 during the lancing process. It can further comprise a ramp-free sample hold zone 208 that can contact the sample hold cam follower 156 and can maintain the test element 114 at a constant partial penetration depth in the skin during the sample collection process, and a retraction ramp 210 that can return the cam slider 154 and the test element 114 to the measuring position in which the test element 114 can be withdrawn from the skin. The time delay damper 142 can slow the cam rotor rotation rate during the sample collection process to extend the sample collection time.

This arrangement can allow precise control of the puncturing and sample collection movement of the test element including a forward movement phase in a puncturing direction until the pricking tip reaches a point of maximum displacement (controlled by lancing cam 132a) and, after the point of maximum displacement, a reverse movement phase opposite to the puncturing direction during which reverse movement phase (controlled by the sample hold cam 130a and the time delay damper 142) the speed can be reduced as compared to the forward movement phase for allowing suctioning of sample into the sample transfer capillary. Other embodiments are possible, such as, for example, replacing the cam recesses cooperating with a pin-shaped cam follower by some other (protruding) cam profile cooperating with a suitably adapted cam follower.

By adjusting the distance between the two cams 130a and 132a in the axial direction of the rotors 130,132, it can be possible to adjust the longitudinal (axial) position of the lancing element during the rearward phase of the movement as compared to the forward phase thereby allowing independent adjustment of the needle tip position during the "hold and dwell function" (suctioning of sample). This position can in particular be independent from the point of maximum displacement of the lancing element. More details about this aspect of a preferred puncturing and sample collection movement are known in the art, such as what is disclosed in for example, WO 2007/073870.

The spindle 136 of the drive assembly 123 of the analysis system 110 can comprise a male linear to rotary motion screw portion 164 that can engage a matching female screw hole 166 in the rear of the housing 118. Thereby, the spindle 136 can rotate when it is manually moved in the axial direction relative to the housing 118. A manual cocking knob 168 can be attached to the spindle 136 through a rotational connection 170. When the cocking knob 168 is manually pulled and pushed in the axial direction, it can operate as an actuator 124 to effect simultaneous axial and rotary motion components of the spindle 136.

The spring input member 128, the torsion power spring 126, the sample hold cam rotor 130, the lancing cam rotor 132, the time delay damper 142, the cam slider 154, and the gripper and optical coupling 162 can move axially with the spindle 136. The spring input member 128 can engage with the spindle 136 through the one-way clutch at the interface 138, and can rotate with the spindle when the actuator 124 is pushed forward, thereby tensioning the torsion power spring 126. When the actuator 124 is pulled rearward, the spring input member 128 does not rotate with the spindle 136 since the relative rotation is reversed and the one-way clutch can be disengaged. As will be described in more detail below, these motion components can be utilized to cock the torsion power spring 126, index the drum magazine 114 to the next position, open the magazine compartment seals to ready the test element 116 for use, and engage the gripper and optical coupling 162 with the test element 116.

In one embodiment, the manually generating force required for the drive assembly 123 can be applied to the drive assembly by a reciprocating movement of an actuator which movement can comprise a rearward movement from a home position (actuator pushed fully forwardly) to an extended position (actuator pulled fully rearwardly) and back to the home position. In one exemplary embodiment, the home position can be the storage position of the instrument 113 because in this position it can have the least volume for storage. Furthermore, in this embodiment, each of the rearward and forward movements of the actuator 124 can provide mechanical energy for at least one of the coupling movement, the puncturing and sample collection movement, and the remaganizing movement. In an exemplary embodiment, an indexing movement for indexing the drum magazine 112 can be provided by at least parts of the reciprocating movement of the actuator, as will be described hereafter.

The drive assembly 123 of the analysis system 110 can comprise a drum indexing pawl 172 that can utilize the axial motion component of the spring input member 128 to rotationally index the drum magazine 112 as part of the manual cocking action through the interaction of the pawl tip 174 with cam rotor-like indexing grooves 176 formed on the outer diameter of drum magazine 112. The indexing pawl 172 can cycle axially once during each test cycle as part of the manual spring cocking motion to rotate the drum magazine 112 to bring a new test element 114 into position just prior to the test. It can also move the drum magazine 112 axially to engage a foil opener 192 as described in more detail below. The drum indexing pawl 172 can slide axially in a channel 177 formed in the housing 118, such that it can execute linear axial motions when the spring input member 128 moves axially and contacts lugs 178 and 180 incorporated in the drum indexing pawl 172.

Further, the analysis system 110 can comprise a lancing penetration adjustment element 182 that can control the lancing penetration depth by controlling the axial position of the lancing cam rotor 132 during the lancing operation. The penetration adjustment element 182 can comprise a lug 184 sliding in an axial slot 186 in the housing 118 and a guide ring 188 sliding on the outer diameter of the housing 118. The axial position of the penetration adjustment element can be set by a screw ring or similar device (not shown). Further, a bias spring (not shown) can be employed between the lancing cam rotor 132 and the sample-hold cam rotor 130 to assure continuous contact between the lancing element cam rotor 132 and the lancing element penetration adjustment element 182.

Further, the analysis system 110 can comprise an angular cam rotor stop 190 which can protrude radially inward from the outer wall of housing 118, and can be positioned and dimensioned such that it can stop the cam rotor rotation after the test element 114 is retracted. A foil opener 192 can align with the front opening of the storage compartment 116 of drum magazine 112, such that it can open a foil barrier of the magazine 112 as will be described in more detail below. A lancing orifice 194 surrounded by a rubber cone 196 can provide a skin contact surface 120 and an opening for allowing puncturing of the skin and collection of a fluid sample for analyte measurement. The lancing orifice 194 can be in registry with one of the possible indexing positions of the drum magazine 112. This position can be the piercing position 197.

A drum shaft 198 can provide rotational support and guidance for the drum magazine 112. An opening (not shown) at the front end 119 of housing 118 can allow used drum magazines 112 to be removed and replaced by new magazines. Accommodations for optical and electronic subsystems, batteries, displays, and control interfaces (not shown) can be made within the generally cylindrical pen-like volume of the housing 118.

FIGS. 6a and 6b illustrate a test element 114 in a perspective view and in an exploded view. In one embodiment, the test elements 114 can be integral lancing and analysis elements, each including a lancing portion 114a and an analysis portion 114b. In this embodiment, the lancing portion 114a can be formed by a lancing element 300 having a pricking tip 300a for penetrating the skin of a patient. Furthermore, in this embodiment, an analysis element 301 can be formed by a glucose measurement film 302 containing a reagent system for detecting glucose. The analysis element 301 (i.e., glucose measurement film 302) can comprise a reagent system, which, in this embodiment, can change its color in accordance to the concentration of analyte contained in the body liquid, such as blood glucose.

The sample liquid can be transported from the pricking tip 300a to a reaction site 303, for example, the glucose measurement film 302, via a sample transfer capillary (also designated capillary channel) 305. In one embodiment, the capillary channel can be formed by a slot 304 in a slotted steel needle forming the lancing element 300. The slot 304 within the lancing element 300 can extend to the rear end of the lancing element 300, so that the lancing element can be comprised of two parallel sidewalls joined at the sharp tip 300a of the lancing element 300. The lancing element can be in permanent fluid communication with the reaction site of the analysis element, the capillary channel of the lancing element leading from the tip of the lancing element for transporting sample liquid by capillary forces to the reagent system. No external force or movement is required for this transport.

Such permanent fluid contact may not, however, be mandatory for all. Rather, it can also comprise other embodiments in which lancing elements and analysis elements are separate from each other, but both located in the compartments of a magazine. With such an embodiment, the analysis elements can be fixed in the compartments of the magazine, whereas the lancing elements can be moveable therein for allowing the pricking movement and for bringing the lancing element to a sample transfer position where it can contact the analysis element for the required sample transfer from the lancing element to the analysis element. Such a design is described in more detail in European patent application 07 017 059, filed on Aug. 31, 2007 and corresponding International Patent Application PCT/EP 2008/006588, which are herby incorporated by reference.

The test element 114 can further comprise a test element body 306 as part of its analysis portion 114b. It can serve several functions and may be formed by a plastic material. As a first function, the test element body 306 can allow for an engagement of the gripping means 420 of the drive assembly 123, and, therefore, can comprise an engagement portion formed by gripper notches 310 near the rear end of the test element body. These gripper notches 310 can be designed to leave a rear end protrusion 311, which may be engaged by the gripping means 308.

Further, as a second function, the test element body 306 can be designed to be an optical fiber slider, comprising several optical wave guides 314 (also designated light guides) which in the one embodiment are optical fibers. The test element body 306 can comprise three light guides 314, accessible by an optical port 316 at the rear end of the test element body 306. Two of the light guides 314 can be optical excitation fibers. The third light guide can function as a readout fiber, which may be used to detect light emitted by the glucose measurement film 302. In this embodiment, the film 302, and hence the reagent system, can be (in the assembled status of the test element 114) at a distal end face of the optical wave guide 314. The distal end of the light guide 314 can be arranged at a reaction site at which the reaction of the sample and the reagent system can take place in such a manner that an optical measurement can be carried out. At least a part of the reagents of the reagent system can be fixed at the distal end face of the light guide 314.

In one embodiment, as will be explained in more detail below, the engagement member of the instrument may not only include means for mechanical engagement of the test element 114, but also optical engagement means for optically contacting the optical port 316 at the rear end of the test element 114. This is why it can be designated gripper and optical coupling 162.

Figure 7:
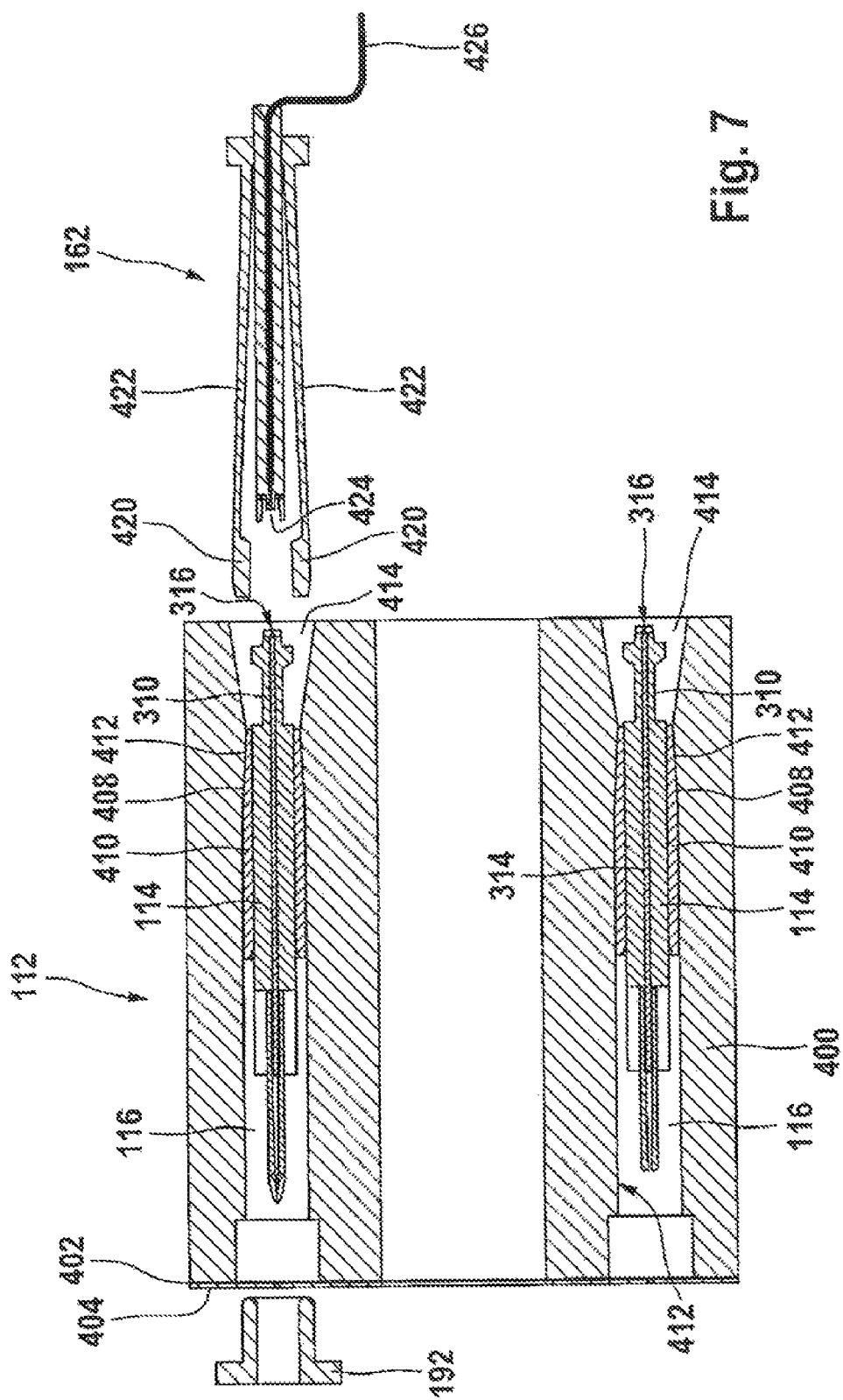
FIG. 7 illustrates a sectional view of a magazine of the analysis system with some parts of the instrument functionally cooperating according to an embodiment of the present disclosure.
Figure 8:
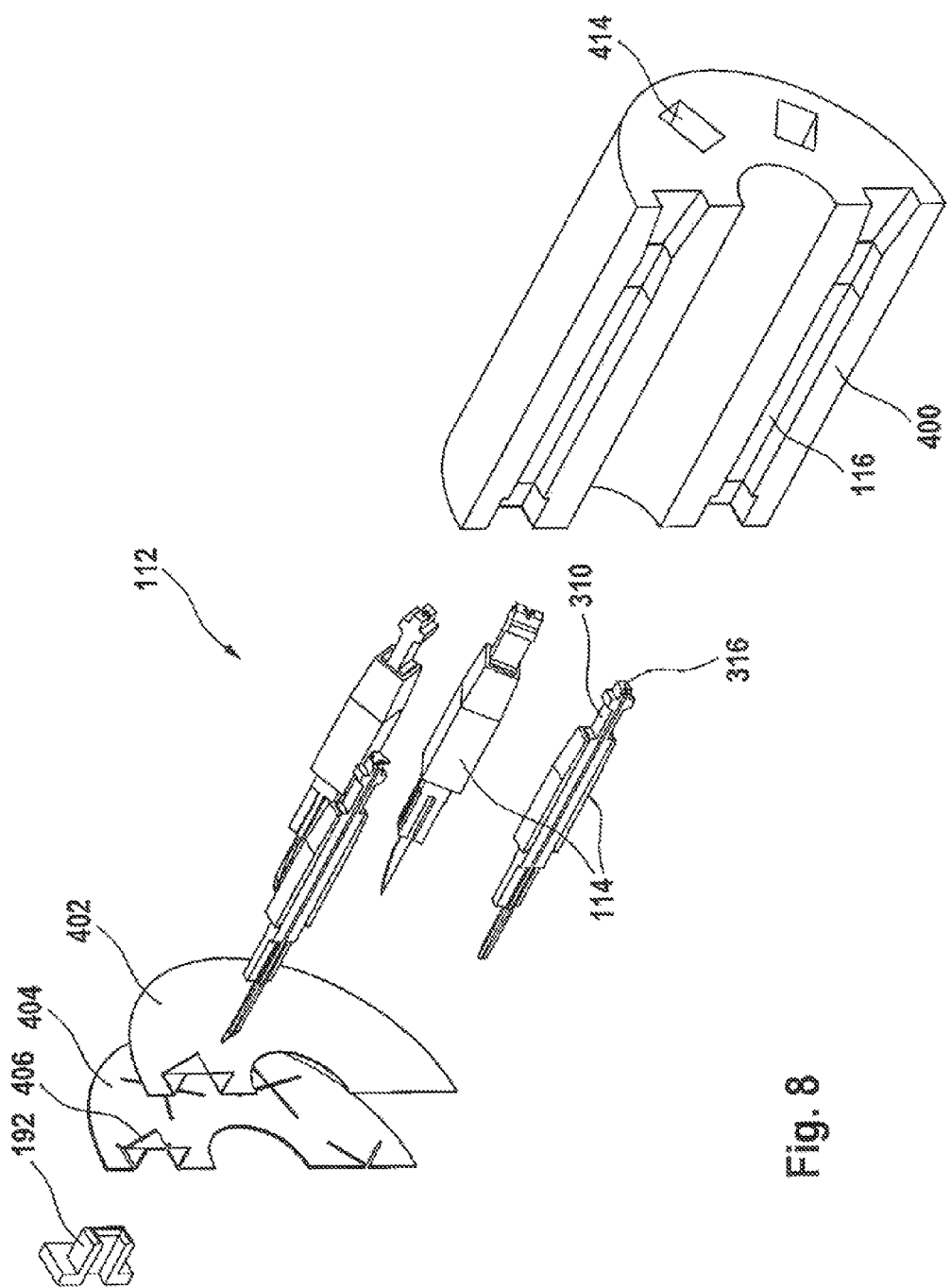
FIG. 8 illustrate a perspective exploded view of a magazine and test elements of the analysis system according to an embodiment of the present disclosure.

Elements of the drum magazine 112, the test element 114, and the gripper and optical coupling 162 are shown in more detail in FIGS. 7 and 8. The drum magazine 112 can comprise a cylindrical drum body 400, that in one exemplary embodiment can be molded from a plastic material containing a desiccant, and further comprising e.g. six axially oriented compartments 116 each comprising a test element 114. A metal foil barrier 402 can close the front of the compartments 116 to exclude moisture and maintain sterility. The foil barrier 402 can be covered by a flexible cap 404 that can contain preformed doors 406 aligned with the compartments 116 that can be pushed open by the foil opener 192 when the drum magazine is moved forward prior to extending the test element 114. The doors 406 can cut and fold the metal foil barrier 402 out of the way, and the open center of the foil opener 192 can provide a passage and guide for the extended test element 114. This can allow to open the foil barrier 402 without contact of the pricking tip 300a of the lancing element 300 therewith. Such contact can be completely avoided during the skin prick analysis operation.

A sealing function at the rear end of the compartments 116 can be provided by a tapered plug seal 408. The test element body 306 can be inserted into a tapered plug sleeve 410 formed at the inner wall 412 of the compartments 116. The tapered plug sleeve can engage a tapered section 412 in the compartment 116 to form the tapered plug seal 408. The tapered plug seals 408 can be engaged in the manufacturing process, and can be released when the test elements 114 are pushed forwardly for the lancing motion. Test element gripper notches 310 that extend rearward from the tapered plug seal 408 can be recessed into access pockets 414 to minimize the chance of accidentally opening the tapered plug seals 408 during handling. The drum magazine 112 and its contents can be sterilized by a penetrating process such as E-beam sterilization after it is sealed.

The gripper and optical coupling 162 can comprise a pair of mechanical grippers 420 carried by flexible arms 422 and an optical coupling 424. The tapered sides of the access pocket 414 can act as guide surfaces to close the mechanical grippers 422 on the test element when the gripper and coupling are advanced into the drum magazine 112 and can engage test element gripper notches 310. Force provided by a spring (not shown) can be used to provide contact between the optical coupling 424 and the optical port 316 at the rear end of the test element body 306. A flexible cable 426 can comprise light guides, electrical conductors or both to functionally connect the optical coupling 424 to the optical and electronic subsystems (not shown) within the housing 118.

The analysis system 110 may further comprise one or more light sources, such as light emitting diodes (LEDs) or laser diodes. These light sources may be located on a stationary structure, such as a printed circuit board, e.g. in contact with or affixed to the housing 118. Further, one or more light detectors may be used, which may also be located inside the housing 118, e.g. on the same printed circuit board, in order to provide for the required signals for the determination of the concentration of the analyte. Light signals may be provided to the optical coupling 424 and the optical port 316 via flexible light guides, which are denoted by referential 426, and which are only schematically depicted. Other types of flexible light guides may be used instead of optical fibers, as described above. The optical light sources may be located on the moving optical coupling in the measuring instrument, and electrical power may be supplied from the stationary portion of the analysis system 110 through flexible electrical conductors. Similarly, the optical light detectors may be located on the moving optical coupling, whereas the electrical power and signal connections are made to the stationary portion of the analysis system 110 through flexible electrical conductors. In a further embodiment, the optical light sources may be located on a stationary structure of the instrument 113, and the light may be conveyed from the moving test element through flexible light guides.

The present disclosure can be suitable for systems in which the measurement quantity which is characteristic for the desired analytical result is an optically measurable quantity and the system can comprise an optical measurement device (such as described above) for measuring the optically measurable measurement quantity. In an exemplary embodiment, a light detector of the optical measurement device can be located in registry with the piercing position such that the change of the measurement quantity of an analysis element fixed in a compartment 116 which can be located in the piercing position can be simply and directly measured thereby. The measurement of the measurable quantity, which can be characteristic for the desired analytical result, can be performed after the remaganizing movement, i.e. with the lancing element inside the magazine compartment 116.

FIGS. 1 and 9 through 13 show multiple views of five steps in the operating sequence. In one exemplary embodiment, the user can load the sealed disposable drum magazine 112 containing test elements 114 into the instrument 113, thereby completing the analysis system 110. FIG. 1 shows the analysis system 110 during the manual cocking process, wherein the manual cocking knob 168 and the spindle 136 can be pulled out to the full extent. During this motion, the spring input member 128, the torsion power spring 126, the sample hold cam rotor 130, the lancing cam rotor 132, the time delay damper 142, the cam slider 154, and the gripper and optical coupling 160 can move axially out (i.e. rearwardly) with the spindle 136, resulting in complete withdraw of the gripper and optical coupling 160 from the drum magazine 112. The one-way clutch (not shown) at the interface 138 between the spring input member 128 and the spindle 136 can prevent reverse winding of the spring during the outward stoke. This motion can further result in the disengagement of the trigger lug 145 of the lancing cam rotor 132 from the annular cam rotor stop 190 of the housing 118, such that the trigger lug 145 can once again engage the release trigger 139. Similarly, this motion can disengage the coupling pin 148 of the time delay damper 142, such that the torsional bias return spring can reset the time delay damper to its initial position. The rear contact lug 180 of the drum indexing pawl 172 can make contact with the rear surface of the spring input member 128 during the same outward motion, and can thereby be pulled back relative to the indexing grooves 176 on the outer diameter of the drum magazine 112. This can result in pulling back the drum magazine 112 from engagement with the foil opener 196, and rotation of the drum magazine 112 such that the next compartment 116 and test element 114 can be brought into the operating position.

Figure 9C:
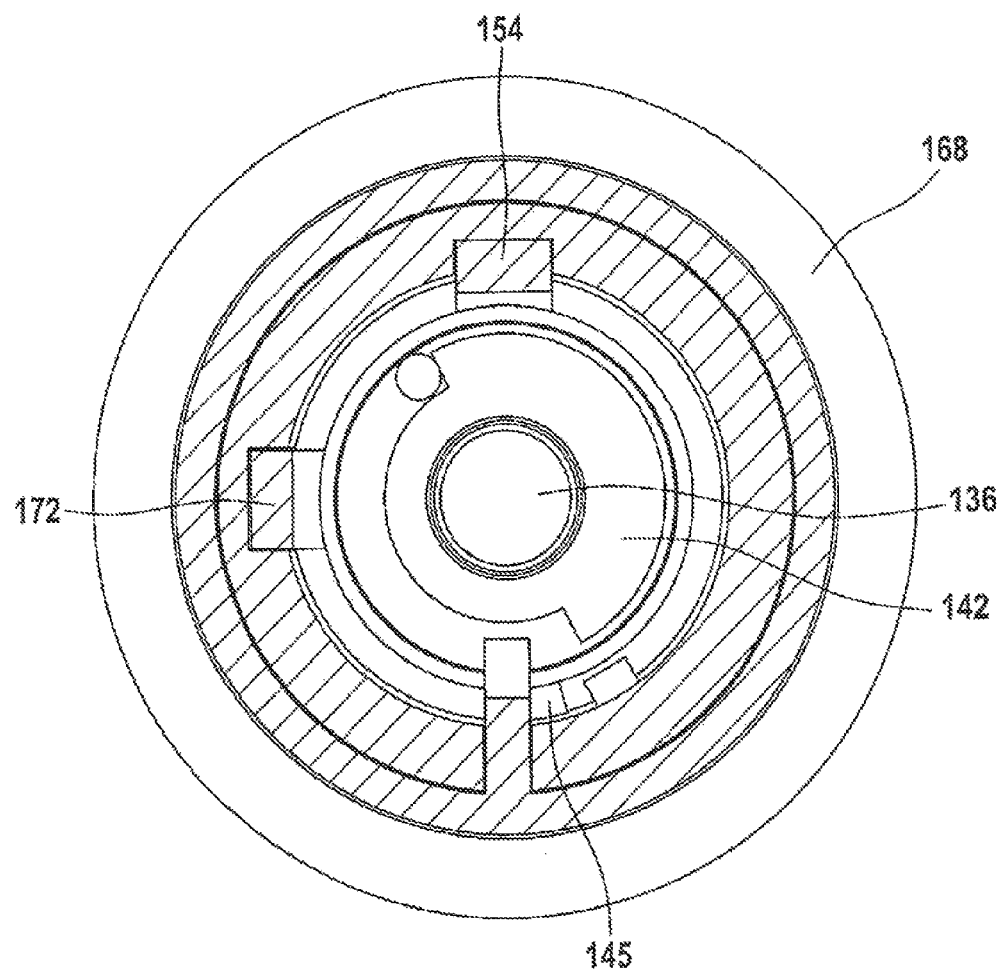

FIG. 9 shows the analysis system 110 at the completion of the manual cocking process, wherein the manual cocking knob 168 and the spindle 136 can be pushed in to the full extent. In this position, the spring input member 128, the torsion power spring 126, the sample hold cam rotor 130, the lancing cam rotor 132, the time delay damper 142, the cam slider 154, and the gripper and optical coupling 160 can be moved axially in (i.e. forwardly) with the spindle 136. In the initial part of this motion, the front contact lug 178 of the drum indexing pawl 172 can contact the front surface of the spring input member 128, and can thereby be pushed forward relative to the indexing grooves 176 and can push the drum magazine 112 forward such that it can engage the foil opener 192. Foil opener 192 can enter the front opening of compartment 116, whereby the preformed doors 406 in the flexible cap 404 can be pushed open. As they open, the doors 406 can cut and fold the metal foil barrier 402 out of the way, and the open center of the foil opener 192 can provide a passage for the extended test element 114. This motion can also reset the indexing pawl 172 to a position in the indexing grooves 176 such that it can be ready to rotate the drum magazine 112 in the next cocking cycle.

In the same axial motion, the gripper and optical coupling 162 can advance into the access pocket 414 and can engage the rear portion of the test element 114, wherein the pair of mechanical grippers 420 carried by flexible arms 422 can contact the tapered sides of the access pocket 414, and can be forced into engagement with the test element gripper notches 310 by cam rotor action. This action can also force the optical coupling 424 into spring-loaded contact with the optical port 316 at the rear end of the test element body 306. Further, motion after engagement of the gripper and optical coupling 162 can unseat the tapered plug seal 408 and can move the test element 114 to the starting position for the lancing motion. This action can be apparent in more detail from FIGS. 7 and 8.

Additionally, in the same axial motion, the male linear to rotary motion screw portion 164 of the spindle 136 can engage the matching female screw hole 166 in the rear of the housing 118 and can rotate, thereby rotating the spring input member 128 through the one-way clutch at the interface 138 and thereby tensioning the torsion power spring 126. Contact between the trigger lug 145 of lancing cam rotor 132 and the release trigger 139 can prevent forward rotation of the linked sample hold cam rotor 130 and the lancing cam rotor 132, thereby countering the torque of the torsion power spring 126.

Figure 10C:
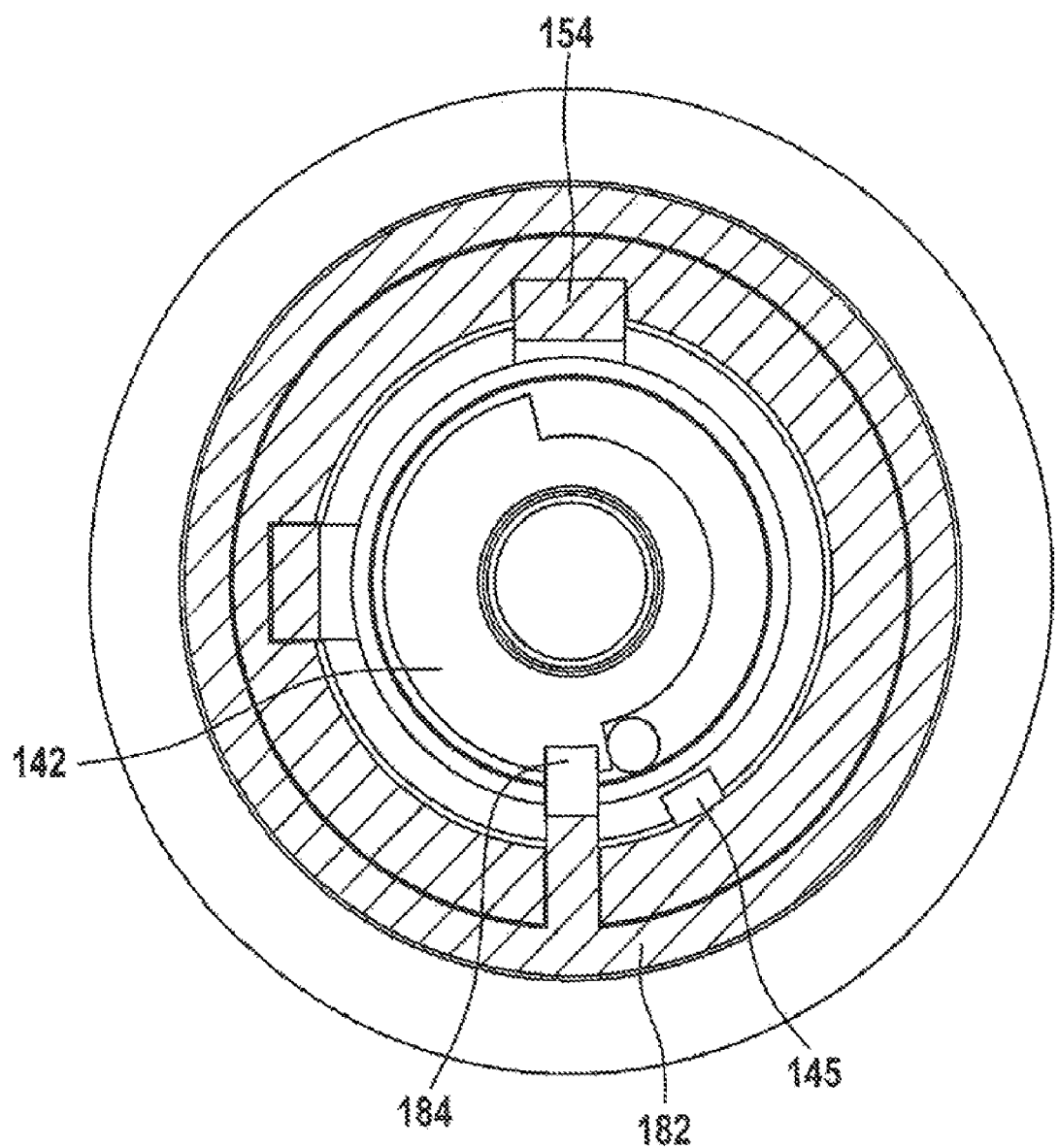

FIG. 10 shows the analysis system 110 at the instant of maximum penetration depth of the lancing element 300. This lancing action can be initiated by the user manually sliding the release trigger 139 such that it can disengage from the trigger lug 145 of the lancing cam rotor 132 and the pre-tensioned torsion power torsion power spring 126 can cause the rotation of the linked sample hold cam rotor 130, the lancing cam rotor 132 and the time delay damper 142. The lift ramp 200 of the lancing cam rotor 132 can contact the lancing cam follower 158 and can accelerate the cam slider 154 forward to cause the test element 114 to penetrate the skin. The maximum penetration of the lancing element can be determined by the axial position of the lancing cam rotor 132, which can be controlled by the position at which the lancing element penetration adjustment element 182 can be set prior to initiating the lancing action.

Figure 11C:
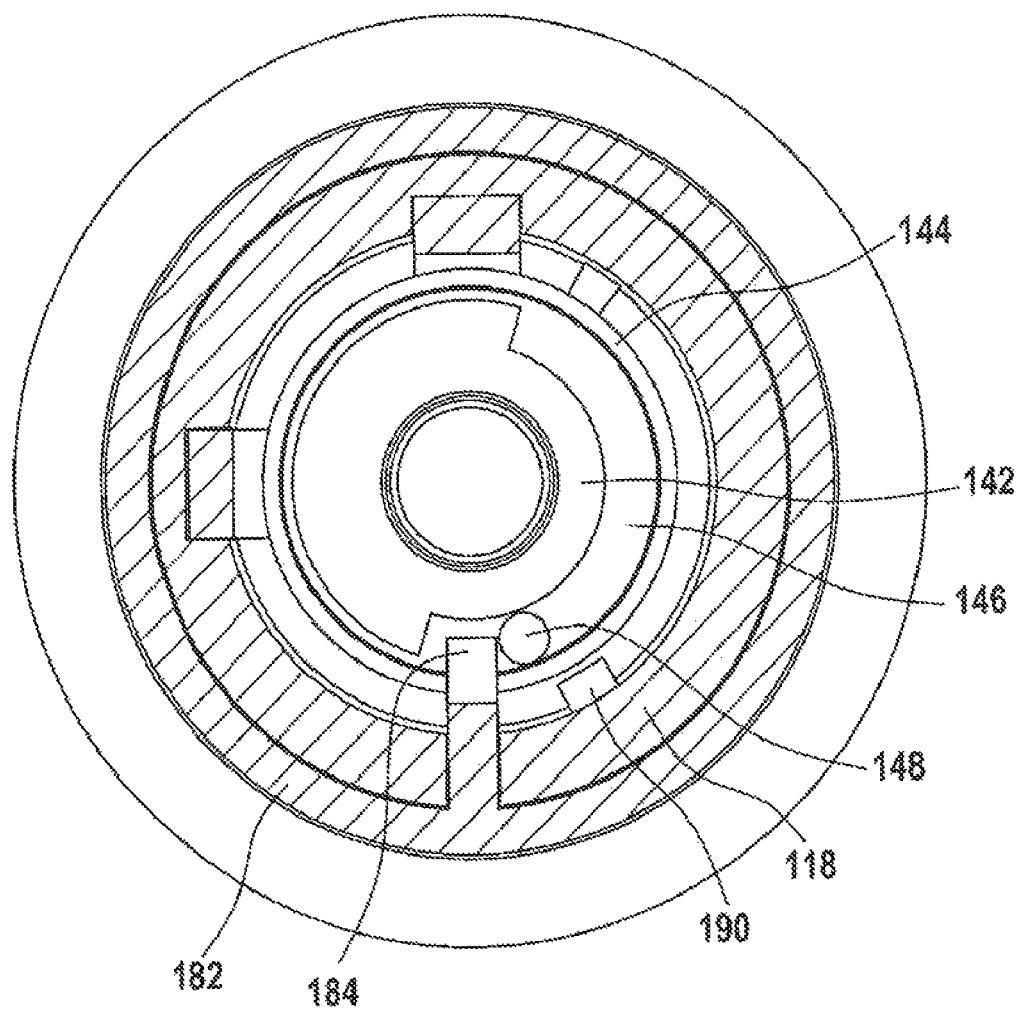

FIG. 11 shows the analysis system 110 at the sample and hold phase. After the maximum penetration, the lancing cam follower 158 can contact the return ramp 202 that stops the test element 114 and can accelerate it back out of the skin. The rearward-moving lancing cam follower 158 can then leave contact with the lancing cam rotor 132 as the lancing cam rotor clearance zone 204 can rotate into alignment, and the sample hold cam follower 156 can contact the ramp-free sample hold zone 208 of the sample hold cam rotor 130. This can halt the rearward motion of the test element 114, and can hold it at a constant partial penetration depth in the skin during the sample collection process as the cam rotor rotation can continue. The time duration of the partial penetration phase can be extended by the time delay damper 142. The coupling pin 148 of the rotating time delay damper 142 can contact the side of the lug 184 of the lancing element penetration adjustment element 182 at the beginning of the partial penetration phase and can stop the rotation of the inner damper rotating member 146. The damper housing 144, which can be affixed to the rotating cam rotors, can continue to rotate causing a relative rotation between the inner damper member 146 and the damper housing 144. This relative rotation can generate a velocity-dependent torque that can slow the cam rotor rotation and thereby can extend the time duration of the partial penetration sample collection phase.

Figure 12C:
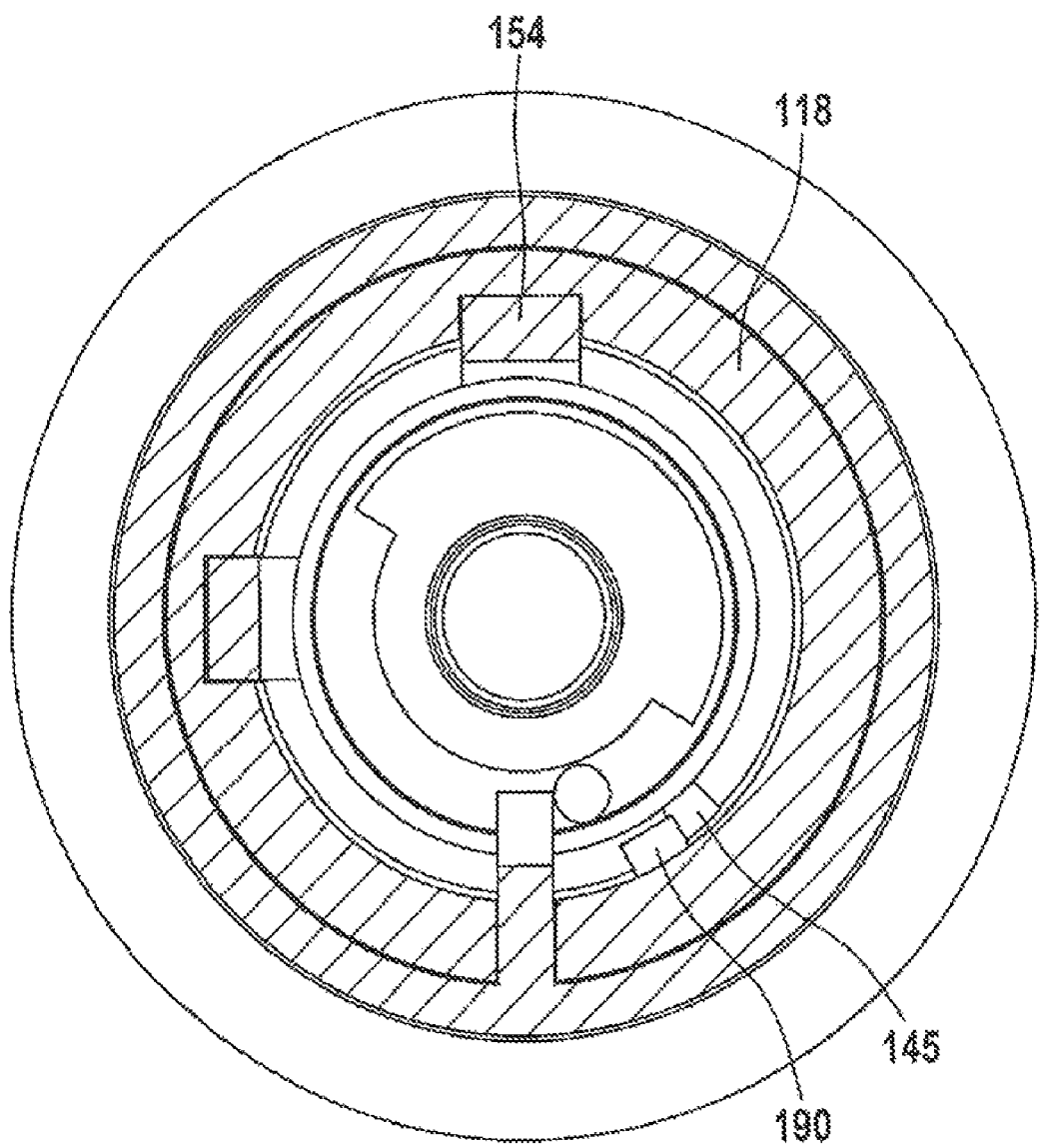

FIG. 12 shows the analysis system 110 in the measuring phase. After the sample collection phase, the retraction ramp 210 of the of the sample hold cam rotor 130 can return the cam slider 154 and the test element 114 to the measuring position, wherein the test element 114 can be withdrawn from the skin. Cam rotor rotation can be stopped when the trigger lug 145 of lancing cam rotor 132 can contact the angular cam rotor stop 190 of the housing 118 after a total cam rotor rotation of e.g. 345 degrees. This can be necessary, since at this time the user may still be holding the release trigger 139 in the release position, in which case it would not engage and stop the trigger lug 145. The final cam rotor rotation of e.g., approximately 15 degrees to bring the trigger lug 145 into contact with the release trigger 139 can take place when the analysis system 110 is cocked for the next use. The cam rotors can rotate about 360 degrees in a complete cycle, but can be stopped at perhaps 345 degrees at the end of the test by the cam rotor trigger lug contacting an angular cam rotor stop. This can be because the user will still have the release trigger pulled, and it will not intercept the cam rotor trigger lug. The final rotation to bring the cam rotor trigger lug back in contact with the release trigger can be part of the cocking operation just prior to the next test.

Figure 13:
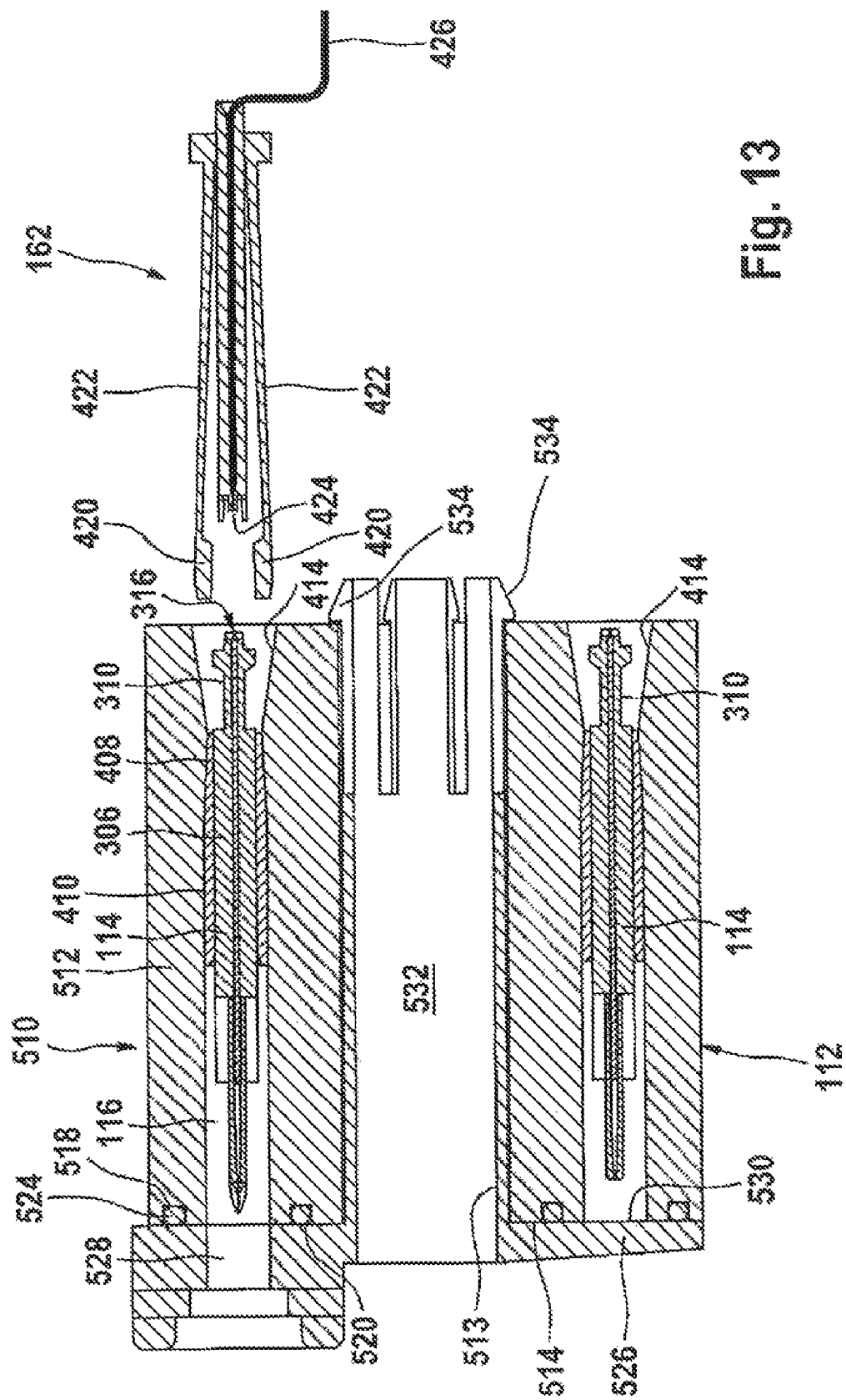
FIG. 13 illustrates a sectional view of a magazine and parts of the instrument functionally cooperating therewith according to another embodiment of the present disclosure.

FIGS. 13 and 14 show an alternative drum magazine 510 in a preferred embodiment of the analysis system 110 that can comprise an alternative means of sealing the compartments 116 containing the test elements 114. The drum magazine 510 can comprise a cylindrical drum body 512 with an axial hole 513, that, in one exemplary embodiment, can be molded from a plastic material containing a desiccant, and further comprising e.g. 6 axially oriented compartments 116 each containing a test element 114. The drum body 512 can also have an end face 514 comprising seal grooves 516, wherein there can be an inner circular seal groove 518, an outer circular seal groove 520, and radial seal grooves 522. The seal grooves 516 can be located such that each opening of the compartments 116 in the end face 514 can be surrounded by seal grooves connecting the inner circular seal groove 518 and the outer circular seal groove 520. The drum body 512 can further comprise a formed rubber sliding seal 524 that can be fitted into the grooves 516 and can be dimensioned such that it can protrude above surface of the end face 514. Seal plate 526 can comprise an open exit port 528 and a planar sealing surface 530. The seal plate 526 can further comprise a spindle 532 with assembly engagement snaps 534 to permit rotation of the drum body 536 about the spindle 532 while maintaining a compressive force between the sealing surface 530 and the sliding seal 524. This can form an effective seal that can close the front of the compartments 116 to exclude moisture and maintain sterility, yet can permit rotation of the drum body 512 and its contents relative to the seal plate 526. Each test element 114 can remain sealed in a separate compartment 116 until it is rotated to the position of the open exit port 528, i.e. the piercing position thereby providing an open passage that can permit lancing and sample collection. If the drum magazine 512 is rotated one half position (e.g. 30 degrees in this example) from this open passage position, all the compartments 116 can be sealed. When the test elements are used step by step portions of the seal plate 526 may be contaminated. However, there is never contact between a compartment 116 containing an unused test element and a contaminated portion of seal plate 526.

A rear sealing function can be provided by a tapered plug seal 408. The test element body 306 can be inserted into a tapered plug sleeve 410 that can engage a tapered section 412 in the compartment 116 to form the tapered plug seal 408. The tapered plug seals 408 can be engaged in the manufacturing process, and can be released when the test elements 114 are pushed out for the lancing motion. The test element gripper notches 310 that can extend rearward from the tapered plug seals 408 can be recessed into access pockets 414 to minimize the chance of accidentally opening the tapered plug seals 408 during handling. The drum magazine 510 and its contents can be sterilized by a penetrating process such as E-beam sterilization after it is sealed. The gripper and optical coupling 162 can comprise a pair of mechanical grippers 420 carried by flexible arms 422 and an optical coupling 424. The tapered sides of the access pocket 414 can act as cam rotor surfaces to close the mechanical grippers 422 on the test element when the gripper and coupling are advanced into the drum magazine 112 and can engage test element gripper notches 310. Force provided by a spring (not shown) can be used to provide contact between the optical coupling 424 and the optical port 316 at the rear end of the test element body 306. A flexible cable 426 can comprise light guides, electrical conductors or both to functionally connect the optical coupling 424 to the optical and electronic subsystems (not shown) within the housing 118.

In summary, a fully automatic finger prick analysis system, of preferably pen-like size and shape, having a volume (of the instrument with a magazine loaded therein) of at most 80 cm$^3$, preferably at most 50 cm$^3$, and a weight of at most 60 g, preferably at most 40 g and, simultaneously, having a very precise control of the lancing action including all required movements is described. The system of the invention can have a drive assembly adapted for driving by manually generated force at least movements of a coupling movement, a puncturing and sample collection movement, and a remaganizing movement. These movements can collectively be designated "mandatory manually driven movements."

The following additional movements ("optional manually driven movements") can be driven by the drive assembly using manually generated mechanical force: 1) An indexing movement of the magazine for transporting a compartment thereof, which compartment can contain an unused disposable test element, to the piercing position. This can be of particular interest if an automatic indexing of the magazine is desired (which may not always the case). 2) A sample transfer movement by which a lancing element can be moved inside the compartment into a sample transfer position in which a sample transfer from the lancing element to the analysis element may be possible. This type of movement may not be provided by the drive assembly if the system comprises an integral lancing and analysis element allowing transport of a sample liquid from its lancing portion to its analysis portion by capillary forces, i.e. without any movement. 3) A foil barrier opening movement for opening a foil barrier provided for preserving sterility of elements (including lancing elements and analysis elements) contained in the compartments of the magazine, can be opened. Such an opening can take place without requiring contact of the pricking tip of the lancing element with the foil barrier.

The force driving the mandatory ("optional manually driven movements") movements and (if applicable) also the force for driving the optional ("optional manually driven movements") movements can be generated by a linear (unidimensional) movement of an actuator. The force generation can take place by pushing the actuator (forwardly) or by pulling the actuator (rearwardly). In one exemplary embodiment, both the pushing and pulling action can be used, each for generating the force required for at least one of the movements.

The term "manually generated force" refers to cases with immediate conversion of a force applied to the actuator into a movement of the respective part or element which needs to be moved and to cases in which the force applied to the actuator can be transformed into stored mechanical energy, in particular by tensioning a spring element. In one exemplary embodiment, the latter may be a metallic spring but also can be some other type of spring device allowing storing of mechanical energy such as, for example, a rubber-elastic element or a gas-compression element can be used.

Not only can the actuation take place in the form of a linear (unidimensional) movement but also the movements driven thereby, i.e. at least one, at least two or all of the following movements can take place in a linear (unidirectional) manner (if applicable in the particular system concerned): the coupling movement, the puncturing and sample collection movement, the remaganizing movement, the indexing movement, the sample transfer movement and the foil barrier opening movement. At least the puncturing and sample collection movement and the remaganizing movement could be parts of an uninterrupted continuous movement. This continuous movement could also include the coupling movement.

The embodiments described above can use a cam rotor and damper to provide the sample hold and dwell function. Other options known in the art are possible and within the scope of the invention. The hold function may be provided by a latch that can stop the test element return motion at the sample hold position, and can then be released after sample collection. In one embodiment, the user can manually release this latch after a few seconds. The analysis system may also signal the user to release the latch with an audible tone or similar means. This signal can be based on time duration or the analysis system sensing the presence of a fluid sample. In another embodiment, an automatically operated latch, e.g. a solenoid operated latch, may be controlled by the analysis system based on time or fluid sample detection.

In one embodiment, the described drive assembly can allow adaption to many different shapes of a "lancing curve" describing the movement of a lancing element over time as required by the particular G&M process. For example, the constant sample collection phase (without movement of the lancing element) can be replaced by a slow movement, preferably against the puncturing direction. This can be easily accomplished by replacing the ramp-free sample hold zone of the sample hold cam rotor by a slightly inclined cam section. In another embodiment, the rubber cone forming, in the described embodiment, the skin contact surface of the instrument may be replaced by a hard ring which can have certain advantages concerning the reproducibility of the penetration depth.

While the system described above uses optical test elements, i.e. test elements producing an optical measurement quantity, a change of which is characteristic for the desired analytical result, in another embodiment, the system can also be used with electrochemical analysis elements which are a well known alternative to optical test elements.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An analysis system for automatically performing a skin prick analysis by pricking the skin for producing a sample of body liquid and detecting an analyte contained in the sample, the analysis system comprising:
    a magazine with a plurality of compartments each containing a test element comprising a lancing element and an analysis element, the lancing element having a pricking tip for performing a skin prick and a sample transfer capillary for transfer of sample liquid to the analysis element, the analysis element comprising
        a reagent system which reacts with the analyte contained in the sample causing a measurable change of a measurement quantity characteristic for the desired analytical result, and
    a reusable hand-held instrument having a housing and a drive assembly for driving movements of parts inside the housing for the analysis, wherein the drive assembly drives at least the following movements by a manually generated mechanical force:
        a coupling movement by which one of the lancing elements in a compartment of the magazine and located in a piercing position is coupled to the drive assembly;
        a puncturing and sample collection movement of one of the lancing elements contained in the magazine and coupled to the drive assembly, the puncturing and sample collection movement includes a forward movement phase in a puncturing direction until the pricking tip reaches a point of maximum displacement and, after the point of maximum displacement, a reverse movement phase opposite to the puncturing direction during which reverse movement phase the speed is reduced as compared to the forward movement for allowing suctioning of sample into the sample transfer capillary;
        a remaganizing movement by which the test element is transported back into the compartment of the magazine.

2. The analysis system of claim 1, wherein the drive assembly drives by a manually generated mechanical force an indexing movement of the magazine for transporting a compartment containing an unused test element to the piercing position.

3. The analysis system of claim 1, further comprising, test elements which are integral lancing and analysis elements including a lancing portion with the lancing element and an analysis portion with the analysis element, the analysis portion of the test elements comprise a reaction site containing the reagent system, wherein the lancing element is in permanent fluid communication with the reaction site of the analysis element, a capillary channel leading to the reaction site for transporting sample liquid by capillary forces to the reagent system.

4. The analysis system of claim 3, wherein the analysis portion of the test element comprises an optical wave guide having a distal end arranged at the reaction site for carrying out an optical measurement.

5. The analysis system of claim 4, wherein at least a part of the reagents of the reagent system are fixed at a distal end face of the optical wave guide.

6. The analysis system of claim 1, wherein the analysis elements are separate from the lancing elements and fixed in the compartments of the magazine and the sample liquid is transferred inside the compartment from the lancing element to the analysis element as a result of a movement of the lancing element, which movement is driven by the drive assembly by manually generated force and brings the lancing element to a sample transfer position in which it contacts the analysis element for sample transfer.

7. The analysis system of claim 6, wherein the measurement quantity characteristic of the desired analytical result is an optically measurable quantity and the system comprises an optical measurement device for measuring the optically measurable measurement quantity, and wherein a light detector of the optical measurement device is located in registry with the piercing position such that the change of an optical measurement quantity of an analysis element fixed in a compartment located in the piercing position can be measured thereby.

8. The analysis system of claim 1, wherein the magazine is a drum magazine.

9. The analysis system of claim 1, wherein the compartments of the magazine comprise at least one barrier to preserve sterility of elements contained therein and to exclude environmental contaminants, the at least one barrier includes at least one of, a foil barrier covering an opening of the compartment, and a tapered plug seal between the test element and a wall of the compartment.

10. The analysis system of claim 9, wherein the instrument comprises a foil opener for opening a foil barrier of the compartment, such that the opening of the foil barrier takes place independently of the lancing element, a movement required for opening of the foil barrier being driven by the drive assembly by manually generated force.

11. The analysis system of claim 1, wherein manually generated force is applied to the drive assembly by a reciprocating movement of an actuator, the reciprocating movement of the actuator comprising a rearward movement from a home position against the puncturing direction to an extended position and a forward movement in the puncturing direction towards the home position, and the re-usable hand-held instrument is stored with the actuator in the home position.

12. The analysis system of claim 11, wherein each of the rearward and forward movements of the actuator provide mechanical energy for at least one of the coupling movement, the puncturing and sample collection movement and the remaganizing movement.

13. The analysis system of claim 1, wherein the drive assembly comprises a cam controller having two cam drive mechanisms, each cam drive mechanism includes a cam rotor with a cam and a cam follower engaging the cam, such that a first part of the movement of the lancing element is determined by a relative movement between the cam follower and the cam of one of the cam drive mechanisms and a second part of the movement of the lancing element is determined by a relative movement of the cam follower and the cam of the other cam drive mechanism.

14. The analysis system of claim 13, wherein distance of the two cams is adjustable in the axial direction of the rotors for adjustment of the rearward phase of the movement of the lancing element.

15. The analysis system of claim 1, wherein the volume of the housing of the re-usable hand-held instrument is approximately 80 cm$^3$.

16. The analysis system of claim 1, wherein the volume of the housing of the re-usable hand-held instrument is approximately 50 cm$^3$.

17. The analysis system of claim 1, wherein the weight of the re-usable handheld instrument with a magazine inserted therein is approximately 60 g.

18. The analysis system of claim 1, wherein the weight of the re-usable handheld instrument with a magazine inserted therein is approximately 40 g.

19. The analysis system of claim 1, wherein a measurement of the measurable quantity characteristic of the desired analytical result is performed after the remaganizing movement.

* * * * *